(12) United States Patent
Vojdani

(10) Patent No.: US 8,663,911 B2
(45) Date of Patent: Mar. 4, 2014

(54) METHOD FOR DETECTION OF INTESTINAL, AND BLOOD-BRAIN BARRIER PERMEABILITY AND TESTING MATERIALS THERETO

(75) Inventor: Aristo Vojdani, Los Angeles, CA (US)

(73) Assignees: Cyrex Laboratories, LLC, Phoenix, AZ (US); Immunosciences Lab, Inc., Los Angeles, CA (US)

( * ) Notice: Subject to any disclaimer, the term of this patent is extended or adjusted under 35 U.S.C. 154(b) by 0 days.

(21) Appl. No.: 13/359,007

(22) Filed: Jan. 26, 2012

(65) Prior Publication Data

US 2012/0196299 A1    Aug. 2, 2012

Related U.S. Application Data

(60) Provisional application No. 61/437,244, filed on Jan. 28, 2011.

(51) Int. Cl.
  *C12Q 1/00*  (2006.01)
  *G01N 33/53*  (2006.01)
  *G01N 33/554*  (2006.01)

(52) U.S. Cl.
  USPC ............... 435/4; 435/7.1; 435/7.2; 435/7.32

(58) Field of Classification Search
  None
  See application file for complete search history.

(56) References Cited

U.S. PATENT DOCUMENTS

2003/0170747 A1   9/2003   Janigro et al.
2010/0190191 A1   7/2010   Dodds

OTHER PUBLICATIONS

Li et al (Infect. Immun. vol. 73, No. 6, pp. 3734-3739, 2005).*
International PCT Search Report and Written Opinion for International Application No. PCT/US2012/022706, Sep. 10, 2012, 9 pages.
Arrieta et al., Alterations in intestinal permeability. *Gut.* 55: 1512-1520, 2006.
Fasano et al., Mechanisms of disease: the role of intestinal barrier function in the pathogenesis of gastrointestinal autoimmune diseases. *Nat Clin Prac Gastroenterol Hepatol.* 2(9): 416-422, 2005.
Fasano, Zonulin and its regulation of intestinal barrier function: the biologial door to inflammation, autoimmunity and cancer. *Physiol Rev,* 91: 151-175, 2011.
Garate et al., Orifin and consequences of brain toll-like receptor 4 pathway stimulation in an experimental model of depression. *J. Neurionflamm.* 8:151, 1-31, 2011.
Morgan et al., Inflammation and dephosphorylation of the tight junction protein occludin in an experimental model of multiple sclerosis. *Neurosci.* 147: 664-673, 2007.
Sapone et al. Divergence of gut permeability and mucosal immune gene expression in two gluten-associated conditions: celiac disease and gluten sensitibity. *BMC Med.* 9: 23, 2011.
Sapone et al., Differential mucosal IL-17 expression in two fliadin-induced disorders: gluten sensitivity and the autoimmune exteropathy celiac disease. *Int Arch Allergy Immunol.* 152: 75-80, 2010.
Shor et al., Gluten sensitivity in multiple sclerosis: experimental myth or clinical truth? *Ann NY Acad Sci*, 1173: 343-349, 2009.
Skardelly et al., Expression of zonulin, c-kit, glial fibrillary acidic protein in human fliomas.*Transl Oncol.* 2: 117-120, 2009.
Vojdani et al., Immune response to dietary proteins, fliadin and cerebellar peptides in childres with autism. *Nutr Neurosci.* 7(3):151-161, 2004.
Walker et al., Epithelial barrier function to antigens. *Ann NY Acad Sco.* 664: 10-17, 1992.
Yacyshyn et al., Multiple sclerosis patients have peripheral blood CD45RO + B cells and increased intestinal permeability. *Dig Dis Sco.* 41(12): 2493-2498, 1996.
Al-Sadi et al., IL-1β causes an increas in intestinal epithelial tight junction permeability. *J. Immunol.* 178: 4641-4649, 2007.
Al-Sadi et al., Mechanism of IL-1β-induced increase in intestinal epithelial tight junction permeability. *J Immunol.* 2008; 180:5653-5661.
Hecht et al., Expression of the catalytic domain of myosin light chain kinase increases paracellular permeability. *Am J Physiol,* 1996; 271:C1678-168.
Ma et al., Cytochalasin B modulation of Caco-2 tight junction barrier: role of myosin light chain kinase. *Am J Physiol,* 2000; 279:G875-G885.
Ma et al., Mechanism of extracellulat calcium regulation of intestinal epithelial tight junction permeability: role of cytoskeletal involvement. *Microsc Res Tech,* 2000; 51: 156-168.
Ma et al., Mechanism of TNF-α modulation of Caco-2 intestinal epithelial tight junction barrier; role of myosin light-chain kinase protein expression. *Am J Physiol,* 2005; 288:G422-G430.
Maes et al., Normalization of the increased translocation of endotoxin from gram negative enterobacteria (leaky gut) is accompanied by a remission of chronic fatigue syndrome. *Neuro Endocrinol Lett,* 2007; 28(6):101-116.

(Continued)

*Primary Examiner* — Albert Navarro
(74) *Attorney, Agent, or Firm* — Fish & Associates, PC

(57) ABSTRACT

Methods, assays, and apparatus are disclosed for testing of antigens associated with intestinal and/or blood-brain barrier permeability. For example, blood, saliva or other bodily fluid can be tested for binding (1) to a bacterial toxin (preferably a lipopolysaccharide), and (2) binding to tissue antigens selected from at least one of (a) a gut-related antigen and (b) a blood brain barrier-related antigen. Analysis of test results can be used to assist in detecting and diagnosing diseases associated with leaky gut syndrome (whether due to paracellular or transcellular pathways, and whether due to bacterial toxins or some other cause) and/or to diseases associated with excessive blood brain barrier permeability, which are contemplated herein to include both neuroinflammation and/or neuroautoimmunity conditions, and especially amyotrophic lateral sclerosis, Parkinsons disease, multiple sclerosis, Alzheimer's, or peripheral neuropathy, and major depression.

4 Claims, 14 Drawing Sheets

(56) References Cited

OTHER PUBLICATIONS

Maes et al., The gut-brain barrier in major depression: intestinal mucosal dysfunction with an increased translocatio of LPS from gram negative bacteria (leaky gut) plays a role in the inflammatory pathophysiology of depression. *Euro Endocrinol Lett*, 2008; 29:117-124.
Matysiak-Budnik et al., Alterations of epithelial permeability by *Helicobacter* and IL-1beta in vitro: protective effect of rebamipide. *Dig Dis Sci*, 2001; 46:1558-1566.
Shen et al., Myosin light chain phosphorylation regulates barrier function by remodeling tight junction structure. *J Cell Sci*, 2006; 119:2095-2106.
Turner, "Putting the aqueeze" on the tight junction: understanding cytoskeletal regulation. *Semin Cell Dev Biol*, 2000; 11:301-308.
Aloisi et al., Regulation of T-cell responses by CNS antigen-presenting cells: different roles for microglia and astrocytes. *Immunol Today*, 2000; 21(3):141-147.
Chen et al., Distruption of tight junctions and induction of proinflammatory cytokine responses in colinic epithelial cells by *Campylobacter jejuni*. *Infect Immun*, 2006; 74:6581-6589.
Engelhardt et al., The ins and outs of the T-lymphocyte trafficking to the CNS: anatomical sites and moleculat mechanisms. *Trends Immunol*, 2005; 29(9):485-495.
Ghirnikar et al., Inflammation in traumatic brain injury: role of cytokines and chemokines. *Neurochem Res*, 1998; 23(3):329-340.
Huang et al., The effects of Fasudil on the permeability of the rat-blood-brain barrier and blood-spinal cord barrier following experimental autoimmune encephalomyelitis. *J Neuroimmunol*. 239: 61-67, 2011.
Juvonen et al., Macromolecular absorption and cow's milk allergy. *Arch Dis Child*, 1990; 65:300-303.
LaPierre, The molecular structure of the tight junction. *Adv Drug Deliv*, 2000; 41:255-264.
Lassmann et al., Microglial cells are a component of the perivascular glia limitans. *J Neurosci Res*, 1991; 28:236-243.
Schneeberger et al., The tight junction: a multifunctional complex. *Am J Physiol Cell Physiol*, 2004; 286:C1213-C1228.
Wong et al., A synthetic peptide corresponding to the extracellular domain of occludin perturbs the tight junction permeability barrier. *J Cell Biol*, 1997; 163(2):399-409.
Biernacki et al., Regulations of the Th1 and Th2 lymphocyte migration by human adult brain endothelial cells. *J Neuropathol Exp Neurol*, 2001; 60(12):1127-1136.
Ganor et al., TCR activation eliminate glutamate receptor GLUR3 from the cell surface of normal human T cells via an autocrine/paracrine granzyme B-mediated proteolytic cleavage. *J Immunol*, 2007; 178:683-6.
Hawkins et al., The blood-brain barrier/neurovascular unit in health and disease. *Oharmacol Rev*, 2005; 57: 173-185.
Kawanokuchi et al., Production and function of IL-17 in macroglia. *J Neuroimmunol*, 2008; 194:54-61.
Kabir H et al., Human TH17 lymphocytes promote blood-brain barrier disruption and central nervous system inflammation. *Nat Med*, 2007; 13:1173-1176.
Kirk et al., Tight junctional abnormality in multiple sclerosis white matter affects all calibers of vessel and is associated with blood-brain barrier leakage and active demyelination. *J Pathol*. 2003; 201: 319-32.
Sospedra et al., Immunology of multiple sclerosis. *Annu Rev Immunol*, 2005; 23:683-747.
Vojdani et al., A gut feeling for immune dysregulation and neuroinflammation. *The Autism File USA*, 2009; 31: 56-64.
Vojdani et al., Antibodies to myelin basic protein, myelin oligodendrocytes peptides, α-β-crystallin, lymphocyte activation and cytokine production in patients with multiple sclerosis. *J Internal Med*. 2003; 254: 363-74.
Wosik et al., Angiotensis II controls occluding function and is requires for blood-brain barrier maintenance: relevance to multiple sclerosis. *J Neurosci*, 2007; 27(34):9032-9042.

Balkovetz, Bacterial invasion of paracellular route: divide and conquer. *Microbes Infect*, 2003; 5:613-619.
Cywes et al., Group A *Streptococcus* tissue invasion by CD44-mediated cell signalling. *Nature*, 2001; 414:648-652.
El Asmar et al., Host-dependent zonulin secretion causes the impairment of the small intestine barrier function after bacterial exposure. *Gastroenterol*, 2002; 123: 1607-1615.
Garrote et al., Celiac disease pathogenesis: the proinflammatory cytokine network. *J Pediatr Gastroenteral Nutr*, 2008; 47:527-532.
Kuula et al., Local systemic responses in matrix metalloproteinase 8-deficient mice during *Porphyromonas gingivalis*- induced periodontitis. *Infect Immun*, 2009; 77(2):850-859.
Leech et al., Persistent endothelial abnormalities and blood-brain barrier leak in primary and secondary progressive multiple sclerosis. *Neuropathol Appl Neurobiol*, 2007; 33: 86-98.
Persidsky et al., Bllod-brain barrier: structural components and function under physiologic and pathologic conditions. *J Neuroimmune Pharmacol*, 2006, 1: 223-236.
Reijerkerk et al., Tissue-type plasminogen activator is a regulator of monocyte diapedesis through the brain endothelial barrier. *J Immunol*, 2008; 181: 3567-3574.
Xu et al., E-cadherin negatively regulated CD44-hyaluronan interaction and CD44-mediated tumor invasion and branching morphogensis. *J Biol Chem*, 2003; 278: 8661-8668.
Ballow, Primary immunodeficiency disorders: antibody deficiency. *J Allergy Clin Immunol*, 2002; 109:581-591.
Chevrier et al., *Boswellia carterrii* extract in hibits the cytokines and promotes th2 cytokines in vitro. *Clin Diag Lab Immunol*, 2005; 575-580.
Cunningham-Rundles et al., Bovine antigens and the formation of circulating immune complexes in selective immunoflobulin A deficiency. *J Clin Invest*, 1979; 64(1): 272-279.
Cunningham-Rundles et al., Milk precipitins, circulating immune complexes, and IgA deficiency. *Proc Natl Acad USA*, 1978; 75(7):3387-3389.
Fagarasan et al., Intestinal IgA syntheses; regulation of front line body defences. *Nat Rev Immunol*, 2003; 3:63-72.
Ford et al., Intestinal sugar permeability relationship to diarrhoeal disease and small bowel morphology. *J Pediatr Gastrointesterol Nutr*, 1985; 4:568-574.
Galdeano et al., The probiotic bacillum *Lactobacillus casei* induces activation of the mucosal immune system through innate immunity. *Clin Vaccine Immunol*, 2006, 13(2):219-226.
Han et al., Xylitol inhibits inflammatory cytokine expression induced by lipopolysaccharides from *Porphyromonas gingivalis*. *Clin Diag Lab Immunol*, 2005; 12(11):1285-1291.
Syrovets et al., Acetyl-boswellic acids inhibit lipopolysacharide-mediated TNF-alpha induction in monocytes by direct interaction with IκB kinases. *J Immunol*, 2005; 174: 498-506.
Wakabayashi et al., Modulation of immunity-related gene expression in small intestine of mice by oral administration of lactoferrin. *Clin Vaccine Immunol*, 2006; 13(2):239-245.
Bjarnason et al. A persistent defect in intestinal permeability in coeliac disease demonstrated by a $^{51}$CR-labelled EDTA absorption test. *Lancet*, 1983; 1:323-325.
Dannaeus et al., Intestinal uptake of ovalbumin in malabsorption and food allergy relation to serum IgG antibody and orally administered sodium cromoglycate. *Clin Allergy*, 1979; 9:263-270.
Davidson et al., Antibodies to maize in patients with Crohn's disease, ulcerative colitis and coeliac disease. *Clin Exp Immunol*, 1979; 35:147-148.
Eterman et al., Wheat grain: a substrate for the determination of gluten antibodies in serum of gluten sensitive patients. *J Immuno Methods*, 1977; 14:85-9.
Gruskay et al., The gastrointestinal absorption of unaltered protein in normal infants and in infants recovering fron diarrhea. *Pediatrics*, 1955; 16:763.
Heyman et al., Intestinal absorption of macromolecules during viral enteritis: an experimental study on rotavirus-infected conventional and germ-free mice. *Pediatr Res*, 1987; 22(1):72-78.
Uhnoo et al., Effect of rotavirus infection and malnutrition on uptake of a dietary antigen in the intestine. *Pediatr Res*, 1990; 27(2):153-1.

(56) References Cited

OTHER PUBLICATIONS

Vojdani et al., The immunology of gluten sensitivity beyong the intestinal tract. *Eur J Inflamm*, 2008; 6(2):1-9.
Vojdani et al., The immunology of ummediate and delayed hypersensitivity reaction to gluten. *Eur J Inflamm*, 2008; 6(1):1-10.
Zanoni G, et al., In celiac disease a subset of autoantibodies against transflutaminase binds toll-like receptor 4 and induces activation of monocytes. *PLoS Med*, 2006; 3(9):1637-1653.
Abrau et al., TLR signaling in the gut in health and disease. *J Immunol*, 2005; 174:4453-4460.
Clayburgh et al., A porous defense: the leaky epithelial barrier in intestinal disease. *Lab Investig*, 2004; 84:282-291.
Fasano et al., *Vibrio cholerae* produces a second enterotoxin, whixch affects intestinal tight junction. *Proc Natl Acad Sci USA*, 1991; 88:5242-5246.
Heyman et al., Macromolecular transport in jejunal mucosa of children with severe malnutrition: a quantitative study. *J Pediatr Gastroenterol Nutr*, 1984; 3:357-363.
Isolauri et al., Antigen absorption in rabbit bacterial diahrrea (RDEC-1). *Dig Dis Sci*, 1990; 35(3):360-366.
Katz et al., Characterization of Porphyromonas gingicalis-induced degradation of epithelial cell junction complexes. *Infect Immun*, 2000; 68(3):1441-1449.
Klatt, Compromised gastrointestinal integrity in pigtail macaques is associated with increased microbial translocation, immune activation, and IL-17 production in the absence of SIV infection. *Mucosal Immunol*, 2010; 3(4):1431-1439.
Obiso et al., The *Bacteroides fragilis* toxin fragilysin disrupts the paracellular barrier of opithelial cells. *Infect Immun*, 1997; 65(4):1431-1439.
Rothman et al., The effect of short-term starvation on mucosal barrier function in the newborn rabbit. *Pediatr Res*, 1985; 19(7):727-731.
Worthington et al., Intestinal absorption of intact proteins in normal and protein-deficient rats. *Am J Clin Nutr*, 1974; 27:276-286.
Wu et al., *Bacteroides fragilis* enterotoxin cleaves the zonula adherens protein, E-cadherin. *Proc Natl Acad Sci*, 1998; 95:14979-14984.
Yuhan et al., Enteropathogenic *E. coli*- induced myosin light chain phophorylation alters intestinal epithelial permeability. *Gastroenterol*, 1997; 113:1873-1882.
Dean et al., Intestinal barrier dysfunction by enteropathogenic *Escherichia coli* is mediated by two effector molecules and a bacterial surface protein. *Milec Microbiol*, 2004; 54(3):665-675.
Guttman et al., Evidence that tight junctions are disrupted due to intimate bacterial contact and not inflammation during attaching and effacing pathogen infection in vivo. *Infect Immun*, 2006; 74(11):6075-6084.
Hecht et al., Clostridium difficule toxin A perturbs cytoskeletal structure and tight junction permeability of clutured human intestinal epithelial monolayers. *J Clin Invest*, 1988; 82:1516-1524.
Monteleone et al., New mediators of immunity and inflammation in inflammatory bowel disease. *Curr Opin Gastroenterol*, 2006; 22:361-364.
Nakamura et al., Cytokine production in patients with inflammatory bowel disease. *Gut*, 1992; 33:933-937.
O'Neill et al., The IL-1 receptor/toll-like receptor superfamily: crucial receptors for inflammation and host defecse. *Immunol Today*, 2000; 21:206-209.
Schiepers et al., Erratum to "Cytokines and major depression" [Prog. Neuropsychopharmacol. Boil. Psychiat. 29(2) (2005) 201-217], *Prog Neuropsychopharmacol Boil Psychiat*, 2005; 29(4):637-638.
Simonovic et al., Enteropathogenic *E. Coli* dephosphorylates and dissociates occludin from intestinal epithelial tight junctions. *Cell Microbiol*, 2000; 2(4):305-315.
Spitz et al., Enteropathogenic *Escherichia coli* adherence to intestinal epithelial monolayers diminishes barrier functions. *Am J Physoil*. 1995; 268:G374-G3.

Suzuki et al., SS1 *Helicobacter pylori* disrupts the paraccellular barrier of the gactric mucosa and leads to neutrophilic gastritis in mice. *Virchows Arch*, 2002; 440:318-324.
Baumler et al., The *Ipf* fimbrial operon mediated adhesion of *Salmonella typhimurium* to murine Peyer's patches. *Proc Natl Acad Sci USA*, 1996; 93:279-283.
Chen et al., Protein kinase C signaling regulates ZO-1 translocation and increased paracellular flux of T84 colonocytes exposed to *Clostridium difficile* toxin A. *J Boil Chem*, 2002; 277(6):4247-4254.
Falker et al., Altered $Ca^{2+}$ regulation of Yop secretion in *Yersinia enterocolitica* after DNA adenine methyltransferase overproduction Is mediated by Clp-dependent degradation of LcrG. *J Bacterial*, 2006; 188(20):7072-7081.
Galan, *Salmonella* entry into mammalian cells: different yet converging signal transduction pathways? *Trends Cell Boil*, 1994; 4:196-199.
Hilbi et al., *Shigella*-induced apoptosis is dependent on caspase-1 which binds to IpaB. *J Biol Chem*, 1998; 273(49):32895-32900.
Kato et al., A new subtype of the metalloprotease toxin gene and the incidence of the three *bft* subtypes among *Bacteroides fragilis* isolates in Japan. *FEMS Microboil Lett*, 2000; 182:171-176.
Nusrat et al., *Clostridium difficile* toxins disrupts epithelial barrier function by altering membrane microdomain localization of tight junction proteins. *Infect Immun*, 2001; 69(3):1329-1336.
Perdomo et al., Polymorphonuclear leukocyte transmigration promotes invasion of colonic epithelial monolayer by *Shigella flexneri J Clin Invest*, 1994; 93:633-643.
Sansonetti, War and peace at mucosal surfaces. *Nat Rev Immunol*, 2004; 4:953-964.
Schulte et al., *Yersinia enterocolitica* invasion protein triggers IL-8 production in epithelial cells via activation of Rel p65-p65 homodimers. *The FASEB Journal*, 2000; 14:1471-1484.
Clemente et al., Enterocyte actin autoantibody detection: a new diagnostic tool in Celiac desease diagnosis, results of a multi-center study. *Am J Gastro*, 2004; 99:1551-6.
Gilot et al., *Listeria monocytogenes* possesses adhesions for fibronectin. *Infect Immun*, 1999; 67(12):6698-6701.
Kong et al.,, Novel role of the vitamin D receptor is maintaining the integrity of the intestinal mucosal barrier. *Am J Physoil Gastrointest Liver Physoil*, 2008; 294: G208-16.
Maes et al., Increased serum IgA and IgM against LPS of enterobacterial in chronic fatigue syndrome (CFS): indication for the involvement of gram-negative interobacterial in the itoilogy of CFS and for the presence of an increased gut-intestinal permeability, *J Affect Disord*, 2007; 99: 237-40.
Menard et al., Multiple facets of intestinal permeability and epithelial handling of dietary antigens. *Mucosal Immunol*, 2010; 3(3): 247-59.
Pentecost M et al., *Listeria monocytogenes* invades the epithelial junctions at sites of cell extrusion. *PloS Pathogens*, 2006; 2(1):0029-0040.
Rauzi et al., Planor polarized actomyosin contractile flows control epithelial junction remodeling. *Nat*, 2010; 468: 1110-4.
Thomas et al., Gliadin stimulation of murine macrophage inflammatory gene expression and intestinal permeability are MYD88-dependent: role of the innate immune system in Celiac disease. *J Immunol*, 2006; 176: 2512-21.
Wang et al., Human zonulin, a potential modulator of intestinal tight junctions. *J Cell Sci*, 2000; 113:4435-40.
Correale et al., The blood-barrier in multiple sclerosis: functional roles and therapeutic targeting. *Autoimmunity.*, 2007; Abstract, 1 page.
Paganelli et al., Isotypic Analysis of antibody response to a food antigen in inflammatory bowel disease. *Intl Arch Allergy Appl Immunol*, 1985; Abstract, 1 page.
Walker et al., Uptake and transport of macromolecules by the intestine. Possible role in clinical disorders, 1974; Abstract, 1 page.
Walker-Smith et al., The spectrum of gastrointestinal allergies to food. *Ann Allergy*, 1984; Abstract, 1 page.
Perdomo et al., Acute Inflammation Causes Epithelial Invasion and Mucosal Destruction in Experimental Shigellosis, *J. Exp. Med.*, 1994, 180:1307-1319.

\* cited by examiner

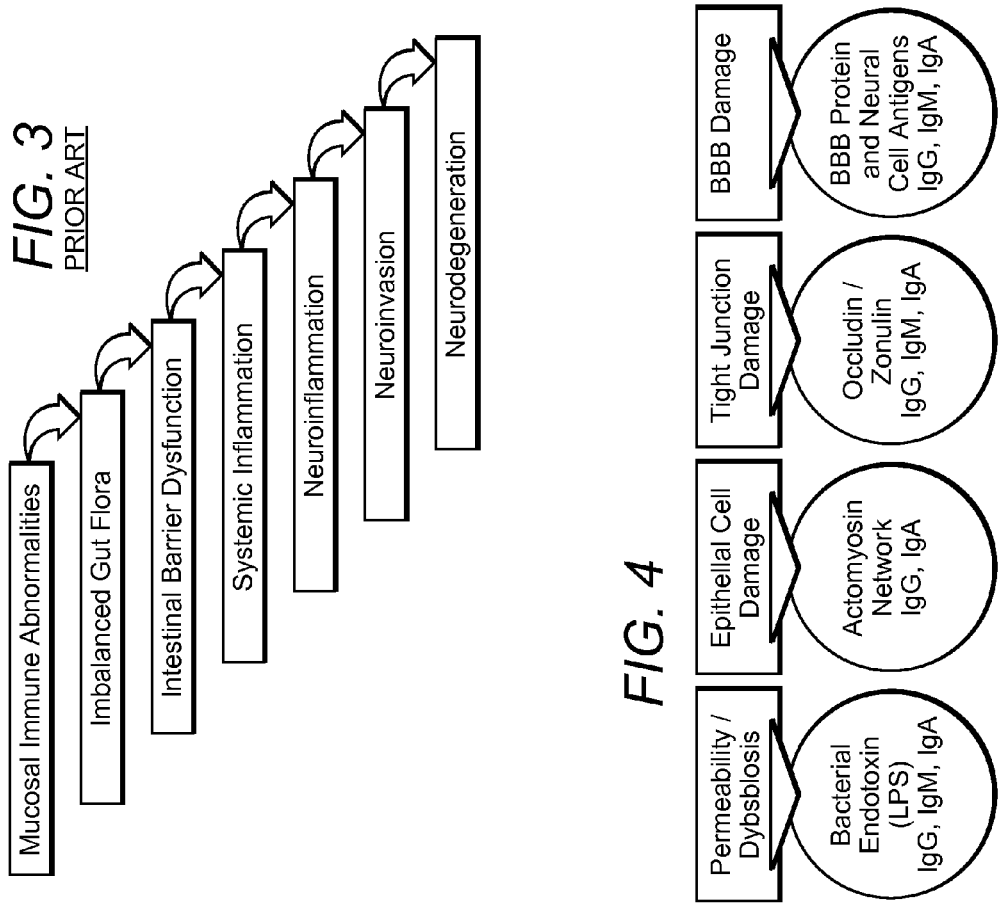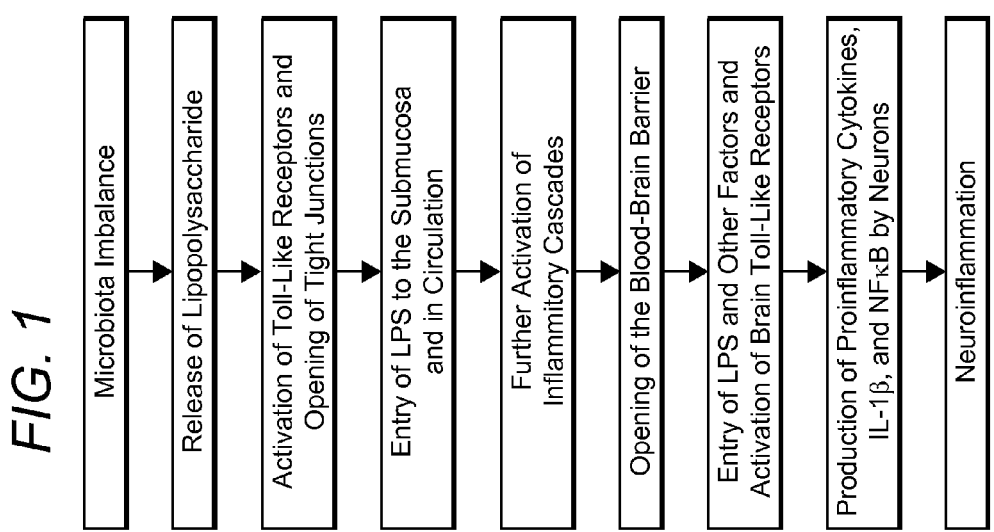

IgG, IgM and IgA antibody levels tested against 12 different antigens representing the environmental factor (LPS), intestinal BBB proteins and associated antigens in healthy subjects #s 1-3

| | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystilin | BBB Protein | Mylin Basic Protein |
|---|---|---|---|---|---|---|---|---|---|---|---|---|
| Cal 1 | 0.743 | 0.752 | 0.532 | 0.764 | 0.551 | 0.535 | 0.757 | 0.762 | 0.542 | 0.763 | 0.546 | 0.78 |
| Cal 2 | 0.658 | 0.678 | 0.539 | 0.694 | 0.542 | 0.539 | 0.677 | 0.688 | 0.543 | 0.695 | 0.556 | 0.703 |
| Sample 1 (OD) | 1.482 | 0.379 | 0.39 | 1.034 | 0.39 | 0.391 | 0.37 | 0.882 | 0.362 | 0.377 | 0.396 | 0.828 |
| | 1.455 | 0.358 | 0.376 | 0.791 | 0.365 | 0.586 | 0.358 | 0.764 | 0.391 | 0.383 | 0.364 | 0.703 |
| Index | 2.10 | 0.52 | 0.72 | 1.25 | 0.69 | 0.91 | 0.51 | 1.14 | 0.69 | 0.52 | 0.69 | 1.03 |
| Sample 2 (OD) | 0.844 | 0.324 | 0.334 | 0.326 | 0.334 | 0.589 | 0.322 | 0.314 | 0.371 | 0.32 | 0.335 | 0.783 |
| | 0.619 | 0.261 | 0.263 | 0.245 | 0.256 | 0.255 | 0.259 | 0.243 | 0.314 | 0.261 | 0.26 | 0.599 |
| Index | 1.04 | 0.41 | 0.56 | 0.39 | 0.54 | 0.79 | 0.41 | 0.38 | 0.63 | 0.40 | 0.54 | 0.93 |
| Sample 3 (OD) | 1.287 | 0.253 | 0.715 | 0.25 | 0.658 | 0.229 | 0.388 | 0.218 | 0.219 | 0.209 | 0.229 | 0.202 |
| | 1.332 | 0.195 | 0.607 | 0.199 | 0.421 | 0.206 | 0.31 | 0.197 | 0.197 | 0.196 | 0.2 | 1.307 |
| Index | 1.87 | 0.31 | 1.23 | 0.31 | 0.99 | 0.41 | 0.49 | 0.29 | 0.38 | 0.28 | 0.39 | 2.24 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 10

IgG, IgM and IgA antibody levels tested against 12 different antigens representing the environmental factor (LPS), intestinal BBB proteins and associated antigens in healthy subjects #s 4-6

| | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystilin | BBB Protein | Mylin Basic Protein |
|---|---|---|---|---|---|---|---|---|---|---|---|---|
| Cal 1 | 0.709 | 0.71 | 0.539 | 0.731 | 0.551 | 0.554 | 0.725 | 0.727 | 0.555 | 0.739 | 0.557 | 0.747 |
| Cal 2 | 0.685 | 0.687 | 0.543 | 0.698 | 0.543 | 0.54 | 0.695 | 0.699 | 0.543 | 0.706 | 0.56 | 0.728 |
| Sample 4 (OD) | 0.244 | 0.557 | 0.265 | 0.244 | 0.692 | 0.278 | 0.262 | 0.529 | 0.433 | 0.292 | 0.479 | 0.308 |
| | 0.221 | 0.525 | 0.207 | 0.233 | 0.501 | 0.22 | 0.22 | 0.488 | 0.488 | 0.196 | 0.492 | 0.21 |
| Index | 0.33 | 0.77 | 0.44 | 0.33 | 1.09 | 0.46 | 0.34 | 0.71 | 0.81 | 0.34 | 0.87 | 0.35 |
| Sample 5 (OD) | 1.276 | 0.189 | 0.206 | 0.2 | 0.2 | 0.17 | 0.199 | 0.199 | 0.182 | 0.183 | 0.195 | 0.175 |
| | 1.317 | 0.229 | 0.233 | 0.228 | 0.234 | 0.279 | 0.231 | 0.216 | 0.216 | 0.228 | 0.224 | 0.235 |
| Index | 1.86 | 0.30 | 0.41 | 0.30 | 0.40 | 0.41 | 0.30 | 0.29 | 0.36 | 0.28 | 0.38 | 0.28 |
| Sample 6 (OD) | 0.237 | 0.477 | 0.236 | 0.395 | 0.231 | 0.219 | 0.661 | 0.232 | 0.676 | 0.226 | 0.228 | 1.185 |
| | 0.198 | 0.426 | 0.202 | 0.365 | 0.233 | 0.194 | 0.493 | 0.202 | 0.495 | 0.192 | 0.2 | 0.796 |
| Index | 0.31 | 0.65 | 0.40 | 0.53 | 0.42 | 0.38 | 0.81 | 0.30 | 1.07 | 0.29 | 0.38 | 1.34 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 11

IgG, IgM and IgA antibody levels tested against 12 different antigens representing the environmental factor (LPS), intestinal BBB proteins and associated antigens in healthy subjects #s 7-9

| | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystillin | BBB Protein | Mylin Basic Protein |
|---|---|---|---|---|---|---|---|---|---|---|---|---|
| Cal 1 | 0.786 | 0.778 | 0.557 | 0.787 | 0.551 | 0.557 | 0.795 | 0.807 | 0.546 | 0.814 | 0.57 | 0.832 |
| Cal 2 | 0.708 | 0.738 | 0.54 | 0.636 | 0.555 | 0.558 | 0.746 | 0.75 | 0.559 | 0.772 | 0.51 | 0.77 |
| Sample 7 (OD) | 0.293 | 0.26 | 0.278 | 0.845 | 0.281 | 0.262 | 0.285 | 0.409 | 0.255 | 0.245 | 0.27 | 0.282 |
| | 0.281 | 0.235 | 0.236 | 0.52 | 0.249 | 0.247 | 0.233 | 0.359 | 0.268 | 0.211 | 0.212 | 0.285 |
| Index | 0.38 | 0.33 | 0.47 | 0.96 | 0.48 | 0.46 | 0.34 | 0.49 | 0.47 | 0.29 | 0.45 | 0.35 |
| Sample 8 (OD) | 0.189 | 0.201 | 0.174 | 0.623 | 0.203 | 0.176 | 0.167 | 0.181 | 0.204 | 0.137 | 0.182 | 0.139 |
| | 0.198 | 0.185 | 0.237 | 0.522 | 0.21 | 0.221 | 0.194 | 0.199 | 0.209 | 0.207 | 0.199 | 0.128 |
| Index | 0.26 | 0.25 | 0.37 | 0.80 | 0.37 | 0.36 | 0.23 | 0.24 | 0.37 | 0.22 | 0.35 | 0.22 |
| Sample 9 (OD) | 1.307 | 0.237 | 0.889 | 0.238 | 0.251 | 0.238 | 0.248 | 0.226 | 0.233 | 0.228 | 0.239 | 1.026 |
| | 1.264 | 0.235 | 0.624 | 0.228 | 0.228 | 0.218 | 0.215 | 0.228 | 0.212 | 0.213 | 0.213 | 0.934 |
| Index | 1.72 | 0.31 | 1.38 | 0.33 | 0.43 | 0.41 | 0.30 | 0.29 | 0.40 | 0.28 | 0.42 | 1.22 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 12

IgG, IgM and IgA antibody levels tested against 12 different antigens representing the environmental factor (LPS), intestinal BBB proteins and associated antigens in patients with celiac disease and gut permeability

| | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystilin | BBB Protein | Mylin Basic Protein |
|---|---|---|---|---|---|---|---|---|---|---|---|---|
| Cal 1 | 0.698 | 0.527 | 0.703 | 0.541 | 0.707 | 0.719 | 0.704 | 0.537 | 0.697 | 0.53 | 0.718 | 0.706 |
| Cal 2 | 0.68 | 0.524 | 0.67 | 0.526 | 0.679 | 0.685 | 0.681 | 0.525 | 0.678 | 0.535 | 0.674 | 0.689 |
| Sample 10 (OD) | 3.789 | 3.741 | 2.146 | 3.745 | 2.31 | 0.466 | 1.217 | 0.758 | 0.598 | 1.285 | 1.009 | 2.127 |
| | 3.8 | 3.769 | 1.896 | 3.762 | 2.089 | 0.39 | 0.975 | 0.921 | 0.528 | 1.166 | 0.98 | 1.695 |
| Index | 5.51 | 7.15 | 2.94 | 7.04 | 3.04 | 0.61 | 1.58 | 1.58 | 0.82 | 2.30 | 1.43 | 2.74 |
| Sample 11 (OD) | 1.396 | 0.621 | 2.017 | 3.11 | 0.694 | 0.418 | 0.53 | 0.419 | 0.495 | 0.406 | 0.466 | 0.444 |
| | 1.237 | 0.572 | 1.973 | 2.713 | 0.651 | 0.393 | 0.444 | 0.453 | 0.455 | 0.442 | 0.375 | 0.433 |
| Index | 1.91 | 1.14 | 2.91 | 5.46 | 0.97 | 0.58 | 0.70 | 0.82 | 0.69 | 0.80 | 0.60 | 0.63 |
| Sample 12 (OD) | 3.56 | 3.775 | 1.454 | 1.943 | 1.985 | 3.765 | 2.012 | 3.827 | 2.674 | 3.713 | 3.76 | 2.02 |
| | 3.648 | 3.773 | 1.727 | 1.941 | 1.952 | 3.735 | 2.012 | 3.837 | 3.498 | 2.894 | 3.789 | 2.051 |
| Index | 5.23 | 7.18 | 2.32 | 3.64 | 2.84 | 5.34 | 2.91 | 7.22 | 4.49 | 6.20 | 5.42 | 2.92 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 13

IgG, IgM and IgA antibody levels tested against 12 different antigens representing the environmental factor (LPS), intestinal BBB proteins and associated antigens in patients with gluten ataxia

| | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystilin | BBB Protein |
|---|---|---|---|---|---|---|---|---|---|---|---|
| Cal 1 | 0.722 | 0.709 | 0.514 | 0.722 | 0.719 | 0.695 | 0.52 | 0.716 | 0.525 | 0.714 | 0.729 |
| Cal 2 | 0.696 | 0.692 | 0.512 | 0.697 | 0.698 | 0.699 | 0.523 | 0.697 | 0.527 | 0.7 | 0.716 |
| Sample 13 (OD) | 1.911 | 0.344 | 1.575 | 0.284 | 3.602 | 3.772 | 3.676 | 1.577 | 3.612 | 0.723 | 3.603 |
| | 1.886 | 0.281 | 1.53 | 0.221 | 3.618 | 3.759 | 3.686 | 1.257 | 3.674 | 0.481 | 3.63 |
| Index | 2.68 | 0.45 | 3.03 | 0.36 | 5.10 | 5.40 | 7.06 | 2.01 | 6.93 | 0.85 | 5.01 |
| Sample 14 (OD) | 1.674 | 0.742 | 0.281 | 1.532 | 2.4 | 2.538 | 1.335 | 3.708 | 1.336 | 3.701 | 0.579 |
| | 1.644 | 0.625 | 0.202 | 1.553 | 1.805 | 2.454 | 1.226 | 3.692 | 1.264 | 3.648 | 0.516 |
| Index | 2.34 | 0.98 | 0.47 | 2.17 | 2.97 | 3.58 | 2.46 | 5.24 | 2.47 | 5.20 | 0.76 |
| Sample 15 (OD) | 1.205 | 0.321 | 0.744 | 0.285 | 3.805 | 3.636 | 0.469 | 0.638 | 3.668 | 1.296 | 1.25 |
| | 1.18 | 0.266 | 0.735 | 0.276 | 3.776 | 3.657 | 0.489 | 0.486 | 3.679 | 1.254 | 1.281 |
| Index | 1.68 | 0.42 | 1.44 | 0.40 | 5.35 | 5.23 | 0.92 | 0.80 | 6.98 | 1.80 | 1.75 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 14

IgG, IgM and IgA antibody levels tested against 12 different antigens representing the environmental factor (LPS), intestinal BBB proteins and associated antigens in patients with multiple sclerosis (MS)

|  | *LPS | Zonulin/ Occludin | Intestine ZOT Receptor | Cell Junction Protein | **MMP 3 | Brain ZOT Binding Protein | Brain ZOT Receptor | Cal-Protection | ***GFAP | α-B Crystilin | BBB Protein |
|---|---|---|---|---|---|---|---|---|---|---|---|
| Cal 1 | 0.692 | 0.498 | 0.493 | 0.705 | 0.69 | 0.694 | 0.506 | 0.697 | 0.519 | 0.704 | 0.723 |
| Cal 2 | 0.649 | 0.469 | 0.508 | 0.721 | 0.721 | 0.721 | 0.516 | 0.719 | 0.54 | 0.726 | 0.748 |
| Sample 16 | 1.855 | 0.445 | 0.349 | 1.447 | 0.546 | 1.478 | 0.508 | 1.287 | 3.705 | 3.804 | 3.834 |
| (OD) | 1.882 | 0.291 | 0.227 | 1.244 | 0.496 | 1.259 | 0.35 | 1.218 | 3.704 | 3.828 | 3.845 |
| Index | 2.79 | 0.52 | 0.58 | 1.89 | 0.74 | 1.93 | 0.84 | 1.77 | 7.00 | 5.34 | 5.22 |
| Sample 17 | 0.467 | 0.266 | 0.244 | 0.385 | 1.235 | 0.517 | 3.677 | 3.653 | 0.525 | 3.834 | 3.782 |
| (OD) | 0.398 | 0.152 | 0.253 | 0.437 | 1.223 | 0.451 | 3.693 | 3.704 | 0.466 | 3.834 | 3.778 |
| Index | 0.65 | 0.30 | 0.50 | 0.58 | 1.74 | 0.68 | 7.21 | 5.20 | 0.94 | 5.36 | 5.14 |
| Sample 18 | 0.618 | 0.353 | 0.221 | 0.662 | 0.587 | 1.226 | 0.405 | 1.273 | 3.665 | 3.84 | 2.721 |
| (OD) | 0.458 | 0.38 | 0.194 | 0.528 | 0.44 | 1.31 | 0.29 | 1.306 | 3.726 | 3.848 | 2.77 |
| Index | 0.80 | 0.52 | 0.41 | 0.83 | 0.73 | 1.79 | 0.68 | 1.82 | 6.98 | 5.38 | 3.73 |

*Lipopolysaccharide  Matrix Metalloproteinase 3 *Glial Fibrillary Acidic Protein $$\text{Index} = \frac{\text{Mean OD of patients}}{\text{Mean OD of calibrators}}$$

FIG. 15

Interpretation of Antibodies Against LPS, Occludin / Zonulin and Actomyoisn Network in Blood

| | | | | | | | |
|---|---|---|---|---|---|---|---|
| LPS IgA | + | + | + | + | − | − | − |
| LPS IgM | + | + | + | − | − | − | − |
| LPS IgG | + | + | + | − | − | − | − |
| Occludin/Zonulin IgG | − | + | + | + | − | − | − |
| Occludin/Zonulin IgM | − | − | + | − | + | − | − |
| Occludin/Zonulin IgA | − | − | + | − | + | − | − |
| Actomyosin IgG | − | − | − | − | − | + | + |
| Clinical Indication | Gut Flora Dybosis | Breakdown in intestinal barrier integrity by bacterial antigens through paracellular pathway | Breakdown in intestinal barrier integrity by bacterial antigens through paracellular pathway | Breakdown in intestinal barrier integrity by factors other than bacterial antigens, through paracellular pathway | Breakdown in intestinal barrier integrity by bacterial antigens through transcellular pathway | | Autoimmunity against muscosal epithelium and other tissue cell cytoskeleton that are found in Chronic Active Hepatitis and primary biliary cirrhosis |

FIG. 16

Interpretation of Antibodies Against LPS, Occludin / Zonulin and Actomyoisn Network in Oral Fluid

| | | | | | |
|---|---|---|---|---|---|
| LPS IgA+IgM | + | − | + | − | − |
| Occludin/Zonulin IgA | − | + | − | − | − |
| Actomyosin IgA | − | − | − | + | + |
| Clinical Indication | Gut Flora Dybosis | Breakdown in intestinal barrier integrity by bacterial antigens through paracellular pathway | Breakdown in intestinal barrier integrity by factors other than bacterial antigens, through paracellular pathway | Breakdown in intestinal barrier integrity by bacterial antigens through transcellular pathway | Autoimmunity against muscosal epithelium and other tissue cell cytoskeletons |

FIG. 17

Interpretation of Antibodies Against LPS, Occludin / Zonulin, Blood Brain Barrier Protein and Neural Antigens in Blood

| | | | | |
|---|---|---|---|---|
| LPS IgA | + | + | - | - |
| LPS IgM | + | + | - | - |
| LPS IgG | + | + | - | - |
| Occludin/Zonulin IgG | - | + | + | - |
| Occludin/Zonulin IgM | - | + | + | - |
| Occludin/Zonulin IgA | - | + | + | - |
| BBB Protein IgG, IgM, IgA | - | + | + | + |
| Neural Antigens IgG, IgM, IgA | - | + | + | + |
| Clinical Indication | Gut Flora Dybosis | Breakdown in intestinal and BBB integrity possibly induced by bacterial toxins, which resulted in neuro-inflammation and neuro-autoimmunity | Breakdown in intestinal and BBB integrity by factors other than bacterial toxins, which resulted in neuro-inflammation and neuro-autoimmunity | Gut Flora Dybosis with or without breakdown in intestinal barrier integrity but with breakdown in BBB which resulted in neuro-autoimmunity | Breakdown in BBB, neuro-inflammation and neuro-autoimmunity with no association with intestinal barrier or gut flora dybosis |

FIG. 18

```
                          SEQUENCE LISTING

<160> NUMBER OF SEQ ID NOS: 3

<210> SEQ ID NO 1
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(30)
<223> OTHER INFORMATION: Calcium binding portion of S100-B

<400> SEQUENCE: 1

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(29)
<223> OTHER INFORMATION: Calcium binding portion of S100-B

<400> SEQUENCE: 2
```

```
Ser Glu Leu Lys Glu Leu Ile Asn Asn Glu Leu Ser His Phe Leu Glu
1               5                   10                  15

Glu Leu Lys Glu Gln Glu Val Val Asp Lys Val Met Glu Thr
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(32)
<223> OTHER INFORMATION: Calcium binding portion of S100-B

<400> SEQUENCE: 3

Leu Asp Asn Asp Gly Asp Gly Glu Cys Asp Phe Gln Glu Phe Met Ala
1               5                   10                  15

Phe Val Ala Met Val Thr Thr Ala Cys His Glu Phe Phe Glu His Glu
            20                  25                  30
```

METHOD FOR DETECTION OF INTESTINAL, AND BLOOD-BRAIN BARRIER PERMEABILITY AND TESTING MATERIALS THERETO

RELATED APPLICATION

The present application claims the benefit of U.S. Provisional Application No. 61/437,244 filed Jan. 28, 2011, which is incorporated herein in its entirety by reference.

FIELD OF THE INVENTION

The present invention relates to methods, assays, and kits for aid in detection and diagnosis of intestinal and blood-brain barrier permeability.

BACKGROUND OF THE INVENTION

Compared to the other cellular organs in the human body, the intestinal epithelial cells are exposed to an enormous number of antigens that originate from ingested foods, yeast, bacteria and viruses. Some of these bacterial antigens pose no threat to the mucosal immune system, while others may be harmful to the host. The intestinal immune system monitors these bacterial antigens in the intestinal lumen by allowing a few molecules to permeate the epithelium, where they interact with the mucosal and systemic immune system, in order to develop regulatory T-cell function or tolerance for these antigens. However, inappropriate or excessive exposure of the intestinal immune system to these bacterial antigens may cause the breakdown of this regulatory mechanism and lead to gastrointestinal disease (1). Therefore, an understanding of the physiology of the antigen uptake is central to an appreciation of the pathogenesis of disease, including inflammatory and autoimmune reactions (2).

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Increased intestinal permeability is thought to be an early stage that precedes the onset of several autoimmune disorders (3-6). For this reason, there has recently been an increased interest in the role of intestinal barrier dysfunction in the pathogenesis of many pathological conditions targeting the GI tract as well as extra-intestinal organs including the nervous system (7). This dysregulation of the intestinal barrier function as the biological doorway to inflammation, autoimmunity and cancer was discussed in a review article by Fasano (7). In this review article, as well as an earlier Fasano article (4), Fasano emphasized that the primary functions of the gastrointestinal tract have traditionally been perceived to be limited to the digestion and absorption of nutrients and to electrolytes and water homeostasis. A more attentive analysis of the anatomic and functional arrangement of the gastrointestinal tract, however, suggests that another extremely important function of this organ is its ability to regulate the trafficking of macromolecules between the environment and the host through a barrier mechanism. Together with the gut-associated lymphoid tissue and the neuroendocrine network, the intestinal epithelial barrier, with its intercellular tight junctions, controls the equilibrium between tolerance and immunity to non-self antigens.

Zonulin/occludin are physiological modulators of paracellular tight junctions that are involved in the trafficking of macromolecules and therefore in the balance between immune response and tolerance (7). When the finely tuned intestinal barrier proteins are dysregulated in those individuals genetically susceptible to environmental factors, the possibility arises for both intestinal disorders such as celiac disease, Crohn's disease and ulcerative colitits, and extra-intestinal autoimmune diseases such as arthritis, lupus, thyroiditis, diabetes, and even multiple sclerosis (MS), malignancies and major depression (8-14). One of the major environmental factors that can contribute to the pathophysiology of gut and brain barrier dysfunction, and hence its involvement in intestinal and extra-intestinal autoimmunities, is bacterial lipopolysaccharides (LPS). Due to gut microbiota dysbiosis and bacterial translocation, LPS is apparently responsible for the activation of toll-like receptors on epithelial cells and activation of an inflammatory cascade which results first in gut barrier and then blood-brain barrier dysfunction (14). The role of LPS in the induction of "leaky gut" and "leaky brain" syndrome is shown in FIG. 1.

FIG. 1 emphasizes that GI tract abnormality can compromise the integrity of the gut barrier and increases the entry of undigested antigens into circulation, thus challenging the immune system. Reaction to these antigens activates immune and inflammatory cascades, resulting in the production of pro-inflammatory cytokines, an array of antibodies, and increased intestinal barrier permeability (or "leaky gut" syndrome). If intestinal barrier dysfunction is left unmanaged, the result could be neuroinflammation, neuroinvasion and neurodegeneration.

Therefore, there is a need for a non-invasive method, apparatus, and assays for the measurement of intestinal permeability to large antigenic molecules that can challenge the immune system, inducing inflammation, which may result in the opening of blood-brain barriers first, followed by neuroinflammation and neurodegenration thereafter (15-25). These needs and others are met by the present invention.

SUMMARY OF THE INVENTION

The inventive subject matter of the present invention provides apparatus, systems, assays and methods in which a sample from a human being can be tested to assist in detection and diagnosis of intestinal and/or blood-brain barrier permeability.

In certain aspects of the present invention, one or more fractions of a sample is/are tested for binding (1) to a bacterial toxin, and (2) binding to a native antigen selected from at least one of (a) a gut-related antigen and (b) a blood brain barrier-related antigen. In certain aspects, the bacterial toxin can advantageously comprise a lipopolysaccharide.

When testing for intestinal permeability, the native gut-related antigen is preferably selected from the list consisting of: (1) an intestinal structural protein; (2) a tight junction protein; (3) a binding receptor to the tight junction protein; and (4) a cell junction protein. In examples of certain aspects of the present invention, testing occurs for antibodies to one or more of actin/actomyosin, occludin and/or zonulin, intestinal ZOT receptor, and matrix metalloproteinase-3 (MMP-3).

When testing for a blood brain barrier permeability, the blood brain barrier-related antigen is preferably selected from the list consisting of: (1) a blood brain barrier protein; (2) a glial fibrillary acidic protein (GFAP); (3) a matrix metalloproteinase (MMP), (4) a brain ZOT binding protein; (5) a brain ZOT receptor; (6) a calprotectin; and (7) a myelin basic protein. In examples of certain aspects of the present invention, testing occurs for antibodies to one or more of (1) a blood brain barrier protein; (2) a glial fibrillary acidic protein (GFAP); and (3) a matrix metalloproteinase (MMP).

From a diagnostic perspective, analysis of test results from one or more of the foregoing described methods can be used to assist in the detection and/or diagnosis of a disease associated with leaky gut syndrome and/or excessive blood brain barrier permeability.

In certain aspects of the present invention, the detection of the samples binding to the respective components can be performed with an immunoassay, including, but not limited to ELISA assay, RIA assay, latex agglutination, beads assay, proteomic assay, and other immunoassays known to one of ordinary skill in the art.

In certain aspects of the present invention, test plates and kits for conducting the immunoassay can also be provided, including for example an improved test plate having as bound peptides: (1) a bacterial toxin; and (2) a native antigen comprising at least one of (a) a gut-related antigen and (b) a blood native brain barrier-related antigen.

In particularly preferred test plates used to assist in the detection and diagnose or otherwise identify a disease associated with leaky gut syndrome, the gut-related antigen can advantageously be selected from the list consisting of: (1) an intestinal structural protein; (2) a tight junction protein; (3) a binding receptor to the tight junction protein; and (4) a cell junction protein.

In particularly preferred test plates used to diagnose or otherwise identify a disease associated with excessive blood brain barrier permeability, the blood brain barrier-related antigen can advantageously be selected from the list consisting of: (1) a blood brain barrier protein; (2) a glial fibrillary acidic protein (GFAP); (3) a matrix metalloproteinase (MMP), (4) a brain ZOT binding protein; (5) a brain ZOT receptor; (6) a calprotectin; and (7) a myelin basic protein.

It is contemplated that test kits can include one or more plates that collectively test for both a first set of antigens associated with leaky gut syndrome and a second set of antigens associated with excessive blood brain barrier permeability.

From a more general perspective, methods and apparatus are contemplated herein for assisting in the detection and diagnosis of a disease associated with excessive permeability of an anatomical barrier, comprising: obtaining and analyzing test results from an antibody test panel that produces signals from binding of a sample from the patient to a bacterial toxin, and a native antigen selected from at least one of (a) a gut-related antigen and (b) a blood native brain barrier-related antigen.

In all of these contemplated methods and apparatus, the samples can comprise any suitable bodily sample, including for example a whole blood sample, a blood serum/sera sample, a saliva sample, or a sample from other bodily fluids.

It is still further contemplated that methods and apparatus contemplated herein can be used to assist in differentially diagnosing diseases related to (1) a gut flora dysbiosis, and (2) a breakdown in intestinal barrier. For example, as currently contemplated, a diagnosis related to gut flora dysbiosis would tend to be indicated when the test results include a positive result for any of IgA, IgM, and IgG to the bacterial toxin of lipopolysaccharide, and negative results for all of IgA, IgM, and IgG to occludin and zonulin, and a negative result for IgG to actomysin.

Differential diagnosis is also contemplated to be aided by distinguishing between a breakdown in intestinal barrier due to a paracellular pathway and a transcellular pathway.

Regarding breakdown through paracellular pathways, a diagnosis related to breakdown in intestinal barrier by bacterial antigens would tend to be indicated when the test results include a positive result for any of IgA, IgM, and IgG to the bacterial toxin of lipopolysaccharide, and positive results for any of IgA, IgM, and IgG to occludin or zonulin, and a negative result for IgG to actomysin. In contrast, a diagnosis related to breakdown in intestinal barrier other than by bacterial antigens would tend to be indicated when the test results include a negative result for all of IgA, IgM, and IgG to the bacterial toxin of lipopolysaccharide, and positive results for any of IgA, IgM, and IgG to occludin or zonulin, and a negative result for IgG to actomysin.

Regarding breakdown through transcellular pathways, a diagnosis related to breakdown in intestinal barrier by bacterial antigens would tend to be indicated when the test results include a positive result for any of IgA, IgM, and IgG to the bacterial toxin of lipopolysaccharide, and negative results for all of IgA, IgM, and IgG to occludin and zonulin, and a positive result for IgG to actomysin.

Also according to the discoveries discussed herein, a diagnosis related to both breakdown in intestinal and blood brain barrier integrity induced by the bacterial toxin would tend to be indicated where the test results include a positive result for any of IgA, IgM, and IgG to the bacterial toxin of lipopolysaccharide, and positive results for any of IgA, IgM, and IgG to occludin and zonulin, a positive result for any of IgA, IgM, and IgG to blood brain barrier proteins, and a positive result for any of IgA, IgM, and IgG to neuronal antigens.

In contrast, a diagnosis related to both breakdown in intestinal and blood brain barrier integrity induced by factors other than the bacterial toxin are likely where the test results include a negative result for each of IgA, IgM, and IgG to the bacterial toxin of lipopolysaccharide, and positive results for any of IgA, IgM, and IgG to occludin and zonulin, a positive result for any of IgA, IgM, and IgG to blood brain barrier proteins, and a positive result for any of IgA, IgM, and IgG to neuronal antigens.

Still further it is contemplated that gut flora dysbiosis can occur without breakdown in intestinal barrier integrity, but with breakdown in the blood brain barrier integrity. For example, a diagnosis related to gut flora dysbiosis in that situation could tend to be indicated where the test results include a positive result for any of IgA, IgM, and IgG to the bacterial toxin of lipopolysaccharide, and negative results for each of IgA, IgM, and IgG to occludin and zonulin, a positive result for any of IgA, IgM, and IgG to blood brain barrier proteins, and a positive result for any of IgA, IgM, and IgG to neuronal antigens.

Similarly, a diagnosis related to breakdown in blood brain barrier integrity, neuroinflammation and neuroautoimmunity, without association with intestinal barrier or gut flora dysbiosis are likely where the test results include a negative result for each of IgA, IgM, and IgG to the bacterial toxin of lipopolysaccharide, and negative results for each of IgA, IgM, and IgG to occludin and zonulin, a positive result for any of IgA, IgM, and IgG to blood brain barrier proteins, and a positive result for any of IgA, IgM, and IgG to neuronal antigens.

Regarding specific diseases, analysis of test results contemplated herein can be used to assist in detecting and diagnosing amyotrophic lateral sclerosis, Parkinsons disease, multiple sclerosis, Alzheimer's, or peripheral neuropathy, and major depression. Such conditions are thought to be likely where the test results include a positive result for any of IgA, IgM, and IgG to blood brain barrier proteins, and a positive result for any of IgA, IgM, and IgG to neuronal antigens.

Various objects, features, aspects and advantages of the inventive subject matter of the present invention will become more apparent from the following detailed description of preferred embodiments, along with the accompanying drawing figures and tables.

BRIEF DESCRIPTION OF THE DRAWINGS

FIG. 1 is a prior art diagram showing a currently understood role of LPS in the induction of leaky gut and leaky brain syndrome.

FIG. 3 is a prior art diagram showing a currently understood etiology of gut to brain dysfunction—how loss of mucosal tolerance, if unmanaged, can trigger a cascade that induces intestinal barrier dysfunction, systemic inflammation, neuroinflammation, neuroinvasion, and neurodegeneration.

FIG. 4 is a diagram showing a proposed scenario of the present invention in which triggers and mechanisms involved in abnormal intestinal permeability and blood brain permeability can be used for a next generation of testing for intestinal permeability identification (IPI) and/or blood brain permeability identification (BBPI).

FIG. 10 shows IgG, IgM and IgA antibody levels tested against 12 different antigens representing the environmental factor (LPS), intestinal and BBB proteins and associated antigens in a first set of three healthy subjects (Samples 1-3), according to certain aspects of the present invention.

FIG. 11 shows IgG, IgM and IgA antibody levels tested against 12 different antigens representing the environmental factor (LPS), intestinal and BBB proteins and associated antigens in a second set of three healthy subjects (Samples 4-6), according to certain aspects of the present invention.

FIG. 12 shows IgG, IgM and IgA antibody levels tested against 12 different antigens representing the environmental factor (LPS), intestinal and BBB proteins and associated antigens in a third set of three healthy subjects (Samples 7-9), according to certain aspects of the present invention.

FIG. 13 shows IgG, IgM and IgA antibody levels tested against 12 different antigens representing the environmental factor (LPS), intestinal and BBB proteins and associated antigens in three patients (Samples 10-12) with celiac disease and gut permeability, according to certain aspects of the present invention.

FIG. 14 shows IgG, IgM and IgA antibody levels tested against 12 different antigens representing the environmental factor (LPS), intestinal and BBB proteins and associated antigens in three patients (Samples 13-15) with gluten ataxia, according to certain aspects of the present invention.

FIG. 15 shows IgG, IgM and IgA antibody levels tested against 12 different antigens representing the environmental factor (LPS), intestinal and BBB proteins and associated antigens in three patients (Samples 16-18) with multiple sclerosis (MS), according to certain aspects of the present invention.

FIG. 16 shows a clinical interpretation of certain antibodies against LPS, occludin/zonulin and actomyosin network in blood, according to certain aspects of the present invention.

FIG. 17 shows a clinical interpretation of elevated levels of certain antibodies against LPS, occludin/zonulin and actomyosin in oral fluid, according to certain aspects of the present invention.

FIG. 18 shows a clinical interpretation of elevated levels of certain antibodies against LPS, occludin/zonulin, blood brain barrier protein and neuronal antigens in blood, according to certain aspects of the present invention.

DETAILED DESCRIPTION OF THE DRAWINGS

Figure 2:
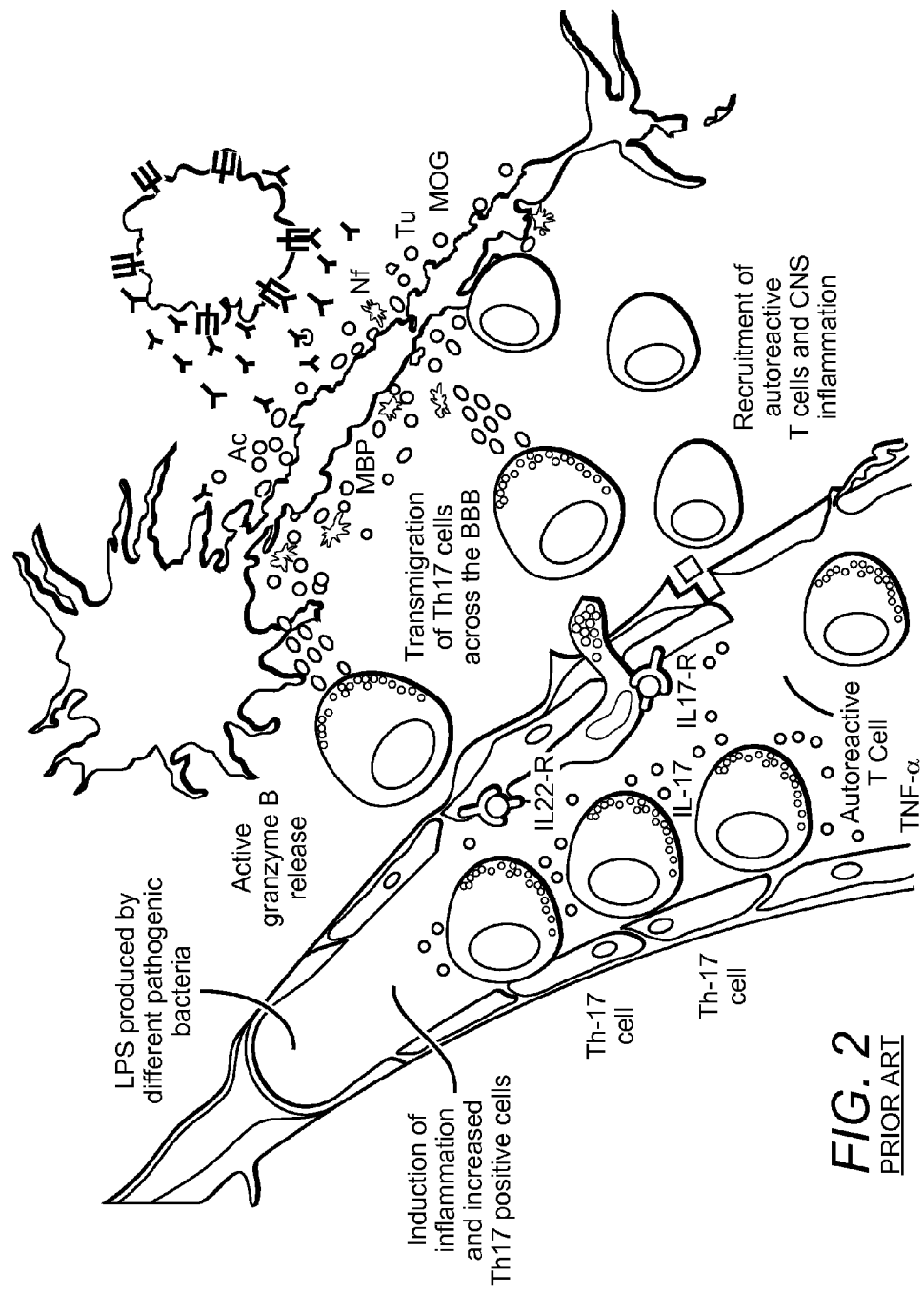
FIG. 2 is a prior art diagram showing a currently understood role of LPS induction of inflammation and activation of Th17 lymphocytes in the pathogenesis of inflammatory and Neuroimmunological disorders: LPS' induction of inflammatory response, production of cytokines, and increase in the number of Th17 positive cells in circulation.

An increased uptake of antigens is a prerequisite for disease development. A number of conditions are known to increase the permeability of the intestine and hence increase antigen uptake. It is likely that the uptake of immunogenic molecules or antigens from the lumen can result in immunological-mediated activity, both within the intestine in the form of IgA and IgM, and beyond the intestine with the production of antigen-specific IgA, IgM, IgG and immune complexes (26, 27).

I. The Effect of Bacterial Toxins and Inflammatory Cytokines on the Induction of Blood-Brain Barrier Disruption and Neuroinflammation The blood-brain barrier (BBB) maintains the internal environment and stability of the central nervous system. Structural and functional changes to the BBB may result in autoimmune diseases, in particular, neuroautoimmune diseases such as multiple sclerosis (28).

The BBB separates blood leukocytes, which normally respond to necrotic injury, from the brain parenchyma where necrotic cell death might take place in response to environmental factors such as infections, toxins, excitotoxicity, or trauma (23). The BBB is composed of two layers. The first layer consists of microvascular endothelial cells, which have abundant tight junctions with structural similarity to that of intestinal epithelial cells (24, 28). The second layer is the glia limitans, which is formed by glial foot processes (29). The perivascular space between the endothelial cells and astrocytes is populated by macrophages, which behave like immature dendritic cells (29). Therefore, factors capable of opening the epithelial TJ barrier are able to destroy both the BBB and neuronal tissue (30-33). This includes bacterial endotoxins, proinflammatory cytokines, enzyme and effector cells Th1, Th17, which are essential to central nervous system inflammation (29, 34-35).

It is firmly established that disruption of the BBB by endotoxins, cytokines, chemokines, adhesion molecules, and others, and the trafficking of autoreactive T-cells from the systemic compartment into the central nervous system, play an important role in the development of MS lesions (36-38). However, when a comparison was made between human Th1 versus Th17 lymphocytes, human Th17 lymphocyte migrated faster across the BBB than Th1 lymphocytes. Indeed a significant number of IL-17- and IL-22-expressing $CD4^+$ $CD45RO^+$ memory lymphocytes upon their migration across BBB expressed $IL-17^+$ and $IL-22^+$ markers, which confirmed the ability of Th17 lymphocytes to cross the BBB in vitro and in vivo (35). The BBB endothelial cells expressed IL-17R and IL-22R, which are used by Th17 lymphocytes to infiltrate the BBB endothelial cells (ECS). This diffusion of cells or antigens, such as bovine serum albumin (BSA), a macromolecule, across the BBB was enhanced significantly when IL-17 and IL-22 were added to monolayers of human BBB-ECS. This enhanced permeability of BBB-ECS correlated with a decrease in the expression of occludin and zonulin, the two important tight junction proteins (39).

These results strongly suggest that inflammation induced by LPS and other bacterial toxins causing activation of Th17 lymphocyte expression of IL-17 and IL-22 receptors on blood-brain barrier endothelial cells results in binding of Th17 to BBB tight junctions. This disrupts the tight junctions, leading to transmigration of Th17 and autoreactive T cells across the BBB, release of granzyme-B by the Th17, and interferon-gamma by CD4 cells, resulting in neuronal cell destruction, release of neuronal cell antigens and BBB proteins into the circulation (the cells co-expressing IL-17, IL-22 and granzyme B through the action of IL-17 and IL-22) play a significant role in the induction and breach in the BBB and the permeabilization of BBB to circulating $CD4^+$ lymphocytes and soluble molecules resulting in CNS inflammation (40-44). The role of Th17 lymphocytes in the pathogenesis of inflammatory and neuroimmunological disorders is shown in FIG. 2. Based on this mechanism of action, bacterial toxin induction of gut permeability and disruption of BBB protein structure can result in antibody production not only against LPS but also against tight junction proteins and BBB proteins. Therefore, steps for tackling neuroinflammation according to certain aspects of the present invention begin with testing for LPS, occludin, claudins, BBB proteins, tight junction protein, enzymes such as matrix metalloproteinase and associated receptor antibodies, based on which clinicians can plan the repair of the gastrointestinal barrier dysfunction, followed by dampening systemic inflammation and ending with the restoration of the blood-brain barrier.

Expression of IL-17 and IL-22 receptors on blood-brain barrier endothelial cells result in the binding of Th17 cells to BBB tight junctions. This disrupts the tight junctions, leading to autoreactive CD4 cells and neurodegeneration. Th17 cells then transmigrate across the BBB, setting the stage for the killing of neurons by the release of granzyme B. This release of neural cell antigens results in a vicious cycle of neuroautoimmunity and neurodegeneration.

Based on information presented here, it is hypothesized that the gut is the starting point for many neurodegenerative disorders. It begins with imbalanced microflora, which releases copious amounts of lipopolysaccharide (LPS). The abundant LPS endotoxins induces up-regulation of proinflammatory cytokines TNF-alpha and IL-1beta, resulting in degradation or dissociation of TJs and their proteins, including occludin and zonulin. This is followed by inflammation in the blood stream which travels to the BBB. The inflammation opens the BBB, causing neuro-infiltration, neuroinflammation, neuroautoimmunity and finally, neurodegeneration. FIG. 3 represents the pathophysiology leading to neurodegeneration; if a person's intestinal barrier dysfunction is not addressed, the person could develop neuroinflammation and possible neurodegeneration over time. Many autoimmune disorders have multiple triggers, symptoms, and system dysfunctions. In cases of neuroautoimmunity, where many of the individuals produce high levels of antibodies to the LPS, TJs, and to the BBB protein, the immune and nervous systems are involved. The common ground for these two systems is the GI tract, the importance of which has been addressed (43).

Therefore, in certain aspects of the present invention, the detection and measurement of antibodies against TJ proteins such as occludin, bacterial endotoxins such as LPS, and BBB proteins is the best way not only to assess GI and intestinal barrier integrity, but also determine and/or diagnose the root cause of systemic inflammation, neuroinflammation, neuroinvasion and neurodegeneration. Also, any lesions of the intestinal epithelium must be quickly repaired. Otherwise, this would allow the penetration of dietary proteins, commensal and pathogenic bacteria into the circulation, driving an inflammatory cascade that would result in complex autoimmune and neuroimmune disorders.

II. Measurement of Permeability to Small Sugars Versus Large Antigenic Molecules The current methodology for assessing intestinal permeability uses lactulose and mannitol. Over the last 40 years, it has been a useful clinical tool. Lactulose absorption suggests a tear in the gut barrier, and thus, intestinal permeability. Against popular belief, the absorption of this small molecule actually indicates a minute leak rather than a tear. Lactulose has relatively low molecular size, and the transfer of this substance through the gut membranes does not reflect the situation for transfer of food or other proteins, and immune response against them. Furthermore, Lactulose/Mannitol test measures the transfer of small molecules only through paracellular but not transcellular pathway.

Therefore, Large Molecule Intestinal Permeability Identification (LMIPI) should be assessed using large molecules such as bacterial endotoxins (comparable to the size of food proteins), which are antigenic and challenge the immune system. Furthermore, in regard to BBB permeability, although several lines of evidence have revealed that alterations in BBB permeability are a primary initiating factor in MS and experimental autoimmune encephalomyelitis (EAE) (45-50), there is currently no recognized blood test for the measurement of BBB permeability. However, in animal models morphological and functional changes in the BBB have been demonstrated by using zonulin/occludin to measure barrier damage impairment (7, 11, 28).

As shown in FIG. 4, the emphasis of the methodology of the present invention is on large molecules that are antigenic and which, upon their release from the barriers, have the capacity to challenge the immune system, resulting in the production of specific IgG, IgM and/or IgA antibodies against them, which are detected in blood, blood serum, and/or saliva samples.

Assessment of intestinal barrier permeability to large antigenic molecules such as bacterial endotoxins and dietary proteins is becoming important in the understanding of the pathogenesis of gastrointestinal and autoimmune diseases. Scientific evidence indicates that many gastrointestinal and autoimmune disorders are accompanied by an increased translocation of endotoxins and other bacterial toxins from aerobic and anaerobic bacteria through the gut wall (7, 51-55). This increased translocation and the inflammation associated with it may induce degradation of tight junction proteins and a subsequent immune response against tight junction proteins such as occludin/zonulin and bacterial endotoxins such as LPS. Indeed, rat and human epithelial cells exposed to bacterial toxins or gliadin secrete a significant amount of zonulin. This release of zonulin is followed by disengagement of the protein ZO-1 from the tight junctional complex, resulting in intestinal permeability through the paracellular pathway (7, 51). And, many chronic conditions are accompanied by increased serum levels of IgA and IgM against LPS and other antigens of pathogenic bacteria (24, 25). These conditions cause gut inflammation and mucosal barrier permeability, whereby enlarged spaces between the cells of the gut wall and dissociation of tight junction proteins can induce losses in the actomyosin network and the protective barrier. This loss of protective barrier may increase bacterial translocation and thus enhance the concentration of serum endotoxins, tight junction proteins, and actomyosin.

According to certain aspects of the present invention, the increased serum IgA and IgM against LPS, tight junction protein (occludin/zonulin) and actomyosin indicate the presence of intestinal barrier permeability and the trafficking of macromolecules across the barriers. The endotoxins of bacteria may be causing the autoimmunity through bacterial toxin acting as a superantigen to T lymphocytes, or by a mechanism called molecular mimicry. Many bacteria have antigenic sites very similar to human tissue antigens, including neuronal tissue. If intestinal barrier permeability is left unchecked, then the inflammatory cascade of antigens and the antibodies produced against them will go in turn into various tissues and trigger first inflammation and then autoimmunity, including neuroautoimmunity. Therefore, if antigenic intestinal barrier permeability is allowed to run its course, the continued degeneration can trigger systemic inflammation, followed by the induction of antigenic and cellular blood brain barrier permeability, bringing concomitant additional immune reactions that result in neuroinflammation, neuroinvasion and neurodegeneration.

Figure 5:
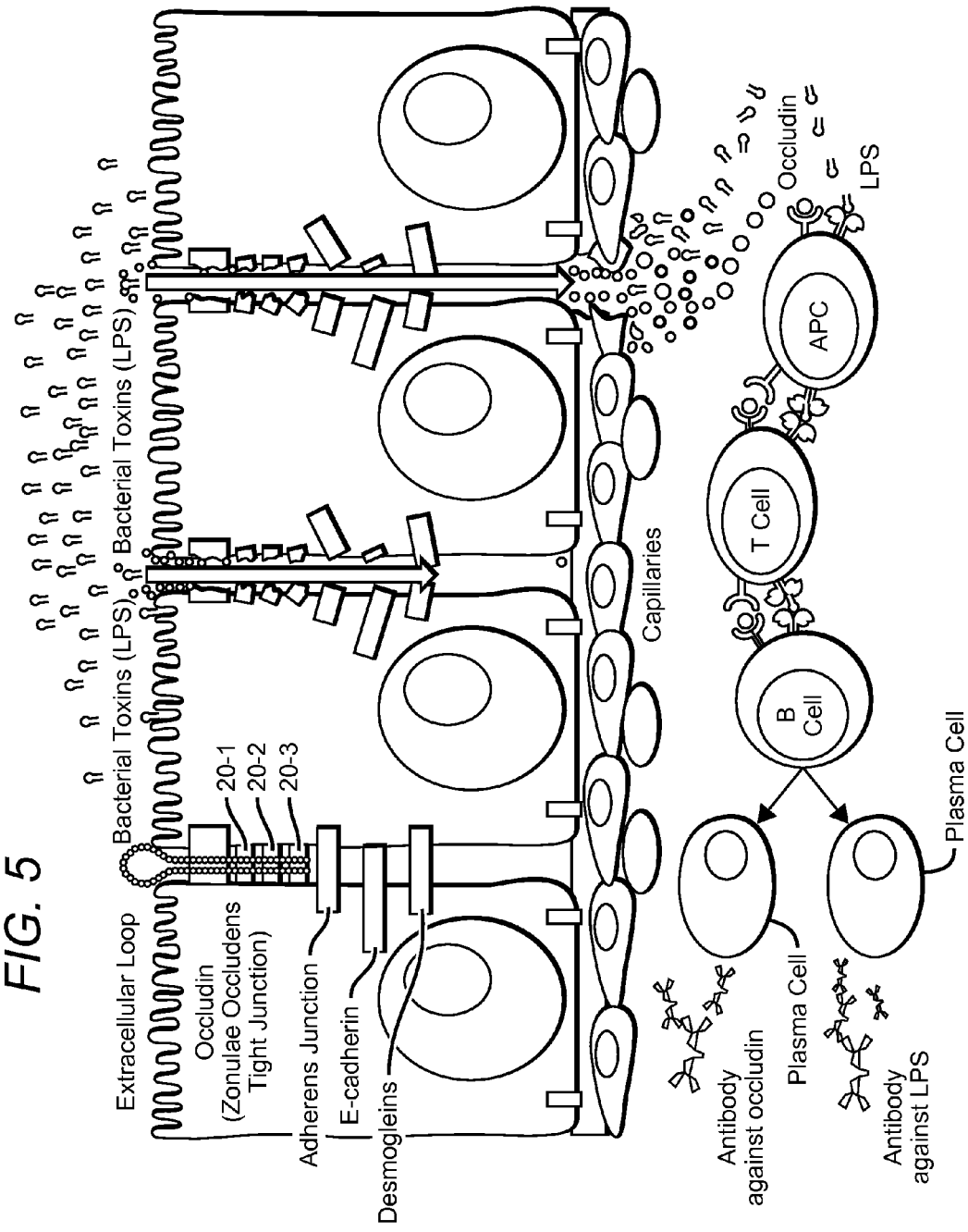
FIG. 5 is a diagram showing a proposed role of abnormal intestinal permeability in the pathogenesis of autoimmune disease according to certain aspects of the present invention.

Thus, according to certain aspects of the present invention, patients with chronic inflammatory and autoimmune conditions should be checked for the existence of increased gut permeability to large antigenic molecules by measurement of IgA, IgG and/or IgM against bacterial LPS, tight junction proteins and actomyosin. Finally, in addition to measurement of IgA, IgG and/or IgM antibodies against LPS and occludin/zonulin, these antibodies should also be measured against BBB proteins, enzymes, associated receptors, and neuronal antigens in patients with neuroimmune disorders. This multistep process of TJ degradation by bacterial toxins and the production of antibodies against released TJ proteins, LPS and other bacterial antigens, which leads to tissue damage and autoimmunity, is illustrated in FIG. 5.

According to certain aspects of the present invention, the detection and measurement of IgA and IgM in oral fluid and IgG, IgM and IgA in blood against TJ proteins and LPS would be the best assay for assessment of intestinal barrier function, while the detection and measurement of LPS, occludin/zonulin and other tight junction proteins, plus BBB proteins and neural cell antibodies (IgG, IgM and IgA) in blood would be the best method for assessment of intestinal/BBB permeability and neuroautoimmunity.

Bacterial antigens (LPS) induce degradation of tight junctions and zonulin release, causing the opening of the tight junctions and the passage of occludin and LPS through the tight junctions and subsequent migration into the submucosa, where the occludin and LPS are presented to macrophages and dendritic cells. Macrophages present these antigens to T and B cells; this is followed by aberrant immune response, both humoral (IgA, IgM and IgG antibodies against occludin and LPS) and cell-mediated. This interplay between humoral and cell-mediated immunity is ultimately responsible for the autoimmune process targeting the intestinal epithelium and other tissue antigens, leading to the tissue damage typical of autoimmune diseases.

Following are exemplary descriptions of assays, and their use and analysis with respect to some test patients. Although other materials and methods similar or equivalent to those described herein can be used in the practice or testing of the present invention, the preferred method and materials now described in the exemplary description of assays to further illustrate the present invention according to certain aspects.

ELISA Assay

A. Materials and Methods—Plate and Sample Preparation:

Lipopolysaccharides from *E. coli* O55:85; *E. coli* K-235, *Pseudomonas aerugmosa, Pseudomonas putida, Salmonella enteritidis, Salmonella typhimurium, Klebsiella pneumonia, Morganella morganii, Hafnia alvei, Citrobacter koseri*, actin, actomyosin, myelin basic protein and a-B crystallin were purchased from Sigma-Aldrich, ST. Louis, Mo. Glial fibrillary acidic protein (GF AP) was purchased from Boehringer Mannheim, Indianapolis, Ind. Also used were zonulin peptides 1, 2, 3, intestinal ZOT receptor, myelin basic protein peptide 87-106, cell 10 junction protein, matrix metalloproteinmase-3, calcium-binding region of S100-B named in this study, BBB-1 MSELEKAMVA LIDVFHQYSG REGDKHKLKK (SEQ ID NO 1), BBB-2 SELKELINNE LSHFLEEIKE QEVVDKVMET (SEQ ID NO 2), BBB-3 LDNDGDGECD FQEFMAFVAM VTTACHEFFE HE (SEQ ID NO 3), brain ZOT binding protein-I, -2, calprotectin (MRP-8), and brain ZOT receptor.

All peptides HPLC grade with purity of greater than 90% were synthesized by EZ Biolab of Carmel, Ind. Throughout this application, unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Figure 6:
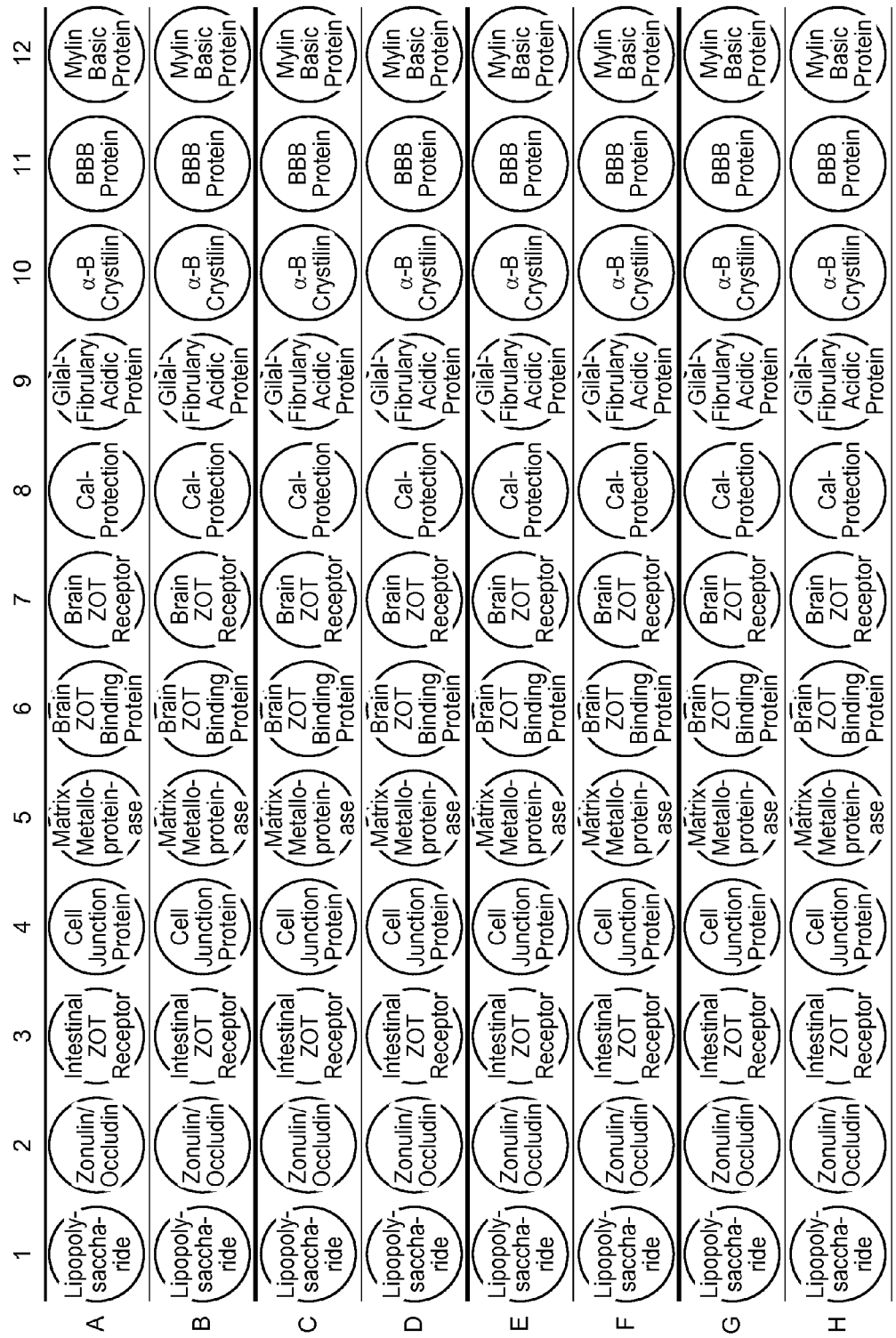
FIG. 6 is a diagram showing the layout of a sample microtiter plate for conducting an immunoassay, the microtiter plate having 12 different rows with 12 different antigens and peptides according to certain aspects of the present invention.

Antigens and peptides were dissolved in methanol at a concentration of 1.0 mg/mL, then diluted 1:100 in 0.1M carbonate-bicarbonate buffer, pH 9.5, and 50 µl were added to each well of a polystyrene flat-bottom ELISA plate, as shown in FIG. 6.

Plates were incubated overnight at 4° C. and then washed three times with 200 µl Tris-buffered saline (TBS) containing 0.05% Tween 20 (pH 7.4). The non-specific binding of immunoglobulins was prevented by adding 200 mL of 2% bovine serum albumin (BSA) in TBS, and incubated overnight at 4° C. Plates were washed and after quality central (QC) were kept at 4° C. until used.

The enzyme conjugates included: Affinity Purified Antibody Phosphatase-labeled Goat anti-Human IgG (Jackson ImmunoResearch, Cat#109-055-008); Affinity Purified Antibody Phosphatase-labeled Goat anti-Human IgA (Jackson ImmunoResearch, Cat#109-055-011); and Affinity Purified Antibody Phosphatase-labeled Goat anti-Human IgM (Jackson ImmunoResearch, Cat. #109-055-043).

Other additional reagents and materials included in the method as further described herein, includes: Phosphate-Buffered Saline Powder (Sigma, Cat#P3813-10PAK), Bovine Serum Albumin (Biocell, Cat#3203-00), Sodium Azide (Sigma, Cat#S-2002), Tween 20 (Sigma, Cat#P1379-1000ML), Glycerol (Sigma, Cat#G5516-500ML), Sodium Hydroxide (Sigma, Cat#S-5881), Magnesium Chloride (Sigma, Cat#8266), Diethanolamine (Sigma, Cat#D-8885), 1.0 N Hydrochloric Acid Solution (Sigma, Cat#H3162-1GA), 5 mg Substrate Tablets: p-NPP (para-nitrophenyl phosphate) (Sigma, Cat#S-0942), and Distilled water (D. $H_2O$).

The microwell plates were prepared and coated with 12 different gut-brain-associated antigens or peptides, as shown in FIG. 6. Calibrator and positive controls and diluted patient samples were added to the wells and autoantibodies recognizing different antigens bind during the first incubation. After washing the wells to remove all unbound proteins, purified alkaline phosphatase labeled rabbit anti-human IgG/IgM/IgA unbound conjugate were removed by a further wash step.

Bound conjugate was visualized with paranitrophenyl phosphate (PNPP) substrate, which gives a yellow reaction product, the intensity of which is proportional to the concentration of autoantibody in the sample. Sodium hydroxide was added to each well to stop the reaction. The intensity of color was read at 405 nm.

Plain red tops or red tiger tops (SST tubes) were used for specimen collection, although in certain aspects, other specimen collection apparatus are contemplated for this assay.

Blood samples were collected using aseptic venipuncture techniques and serum was obtained using standard procedures. In certain aspects, it is preferred that a minimum of 100 microliter of serum for the assay, which therefore corresponds to about one ml or more of blood.

B. Test Assay Procedure

Figure 7:
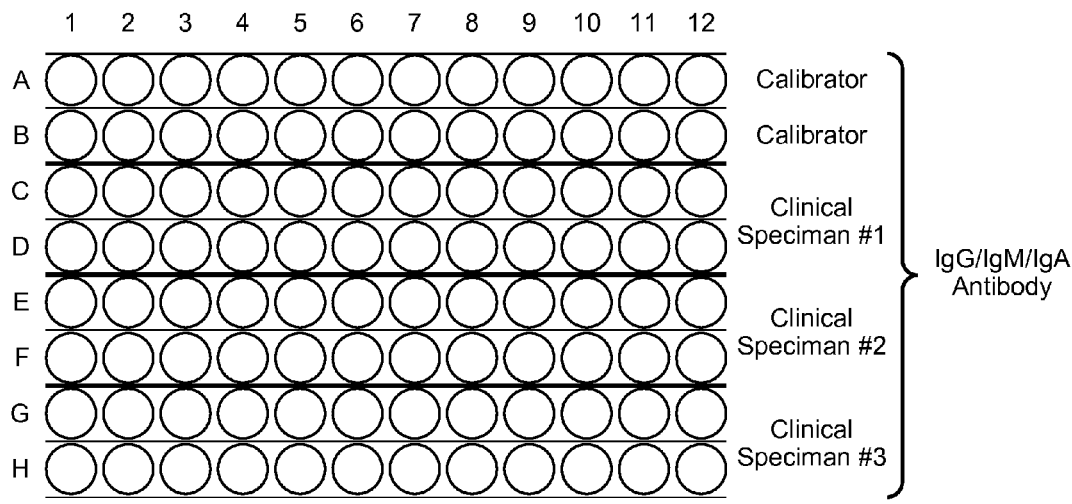
FIG. 7 is a diagram showing the layout of a sample microtiter plate according to certain aspects of the present invention, in which IgG/IgM/IgA is measured against 12 different antigens or peptides from intestinal and BBB protein and associated tissue antigens (bound antigens and peptides are transparent).

The analytical procedure for IgG, IgM, and/or IgA antibody against LPS, intestinal and/or BBB proteins is now discussed. In some aspects, all reagents were allowed to reach room temperature before the test assay was commenced. The test assay procedure includes preparing the desired number of coated wells or plates with the desired number and type of antigens and/or peptides. Once the microtiter wells are prepared, about 100 µl of 1:100 diluted control calibrator are added to Rows A and B of the microtiter plate as shown in FIG. 7, which can be done using a multi-channel pipettor. About 100 µl of 1:100 diluted patient's test sample, here blood serum, was added to duplicate wells of rows C and D for the first Clinical Specimen rows E and F for the second Clinical Specimen and rows G and H for the third Clinical Specimen as shown in FIG. 7.

Figure 8:
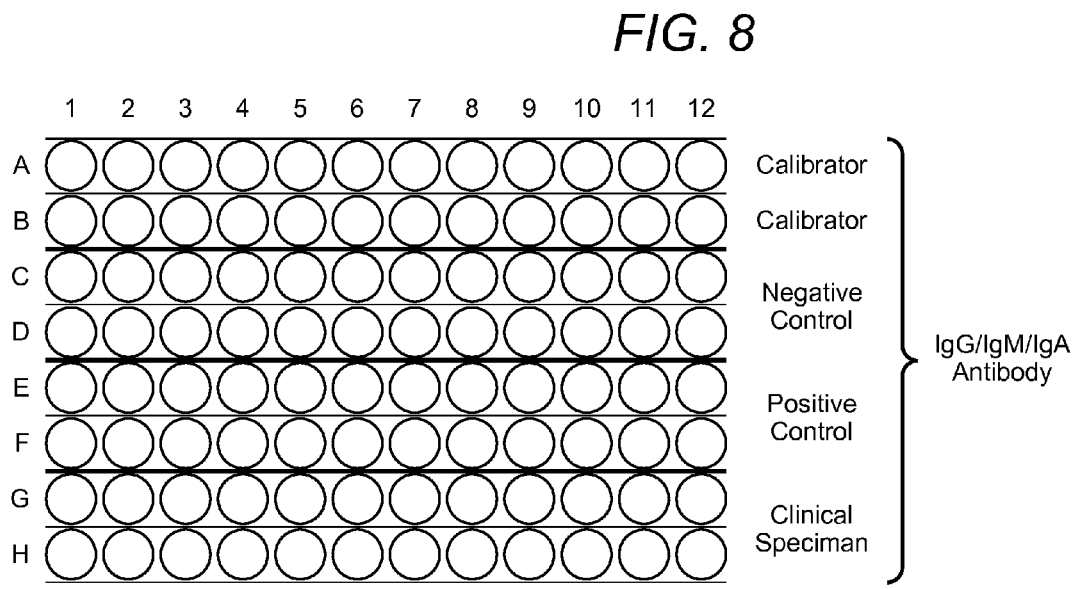
FIG. 8 is a diagram showing the layout of a sample microtiter plate according to certain aspects of the present invention, in which IgG/IgM/IgA is measured with weekly negative and positive controls for quality control purposes (bound antigens and peptides are transparent).

On a separate plate, the periodic (i.e., weekly) negative and positive controls similar to clinical specimens in duplicates were conducted, as shown in FIG. 8.

The plates were then incubated for about 60 minutes at room temperature. After incubation, the wells were then emptied and washed four times with PBS using an ELISA Washer. About 100 µl of optimally diluted alkaline phosphatase-labeled goat anti-human IgA was added to the IgA plate or about 100 µl of enzyme-labeled IgG was added to the IgG plate and anti-IgM was added to the IgM plate at optimal dilution.

The respective plates were then incubated for about 30 to about 60 minutes at room temperature. About ten minutes before the conjugate-incubation ends, a substrate solution was prepared by mixing about 5 mg of p-nitrophenyl phosphate tablet with about 5 ml of substrate buffer, which was mixed well until the tablet completely dissolved. Washing four times with PBS using the ELISA washer was repeated. Then, about 100 µl of substrate solution was added to each well. The plate was then incubated for about 30 minutes at room temperature with the avoidance of any exposure to direct sunlight. The reaction was stopped by adding about 50 µl of 3 N NaOH. The color intensity of the wells were read using a microtiter plate reader at 405 nm against a blank well, with the absorbance values of calibrators, controls and unknown samples being recorded.

C. Calculation of Results

After the plate was read at 405 nm to obtain the optical density values ($OD_{405}$), the mean ODs of the negative controls, the mean ODs of the positive controls and the mean ODs of each clinical specimen were divided by the mean ODs of calibrators on Rows A and B to obtain each Index Value (IV).

The Index Value (IV) for each antibody was calculated against the 12 different antigens by dividing the mean OD of each duplicate sample by the mean OD of the calibrator control value (for example, divide the mean OD of wells C1 and D1 by the mean OD of wells A1 and B1, the mean OD of wells C2 and D2 by the mean OD of wells A2 and B2, the mean OD of wells C3 and D3 by the mean OD of wells A3 and B3, etc.).

The results were then compared to the established reference ranges.

$$Index = \frac{Mean\ OD\ of\ patients}{Mean\ OD\ of\ calibrators}$$

Index calculation for Zonulin/Occludin

| | |
|---|---|
| Cal 1 (OD) | 0.48 |
| Cal 2 (OD) | 0.50 |
| Sample 3 A (OD) | 3.4 |
| Sample 3 B (OD) | 3.2 |
| Index | 6.7 |

D. Interpretation of Results i. Pattern of IgG/IgM/IgA Antibody in Patients with Celiac Disease, Gluten Immune Reactivity and Sensitivity, and Crohn's Disease:

Examples of IgG, IgM, and IgA antibody patterns of 9 healthy subjects (Tables 1-3) and their comparison with 3 patients with celiac disease and intestinal permeability (Table 4), 3 patients with gluten ataxia (Table 5), and 3 patients with multiple sclerosis (Table 6) are shown in Tables 1-6, respectively.

Data interpretation and laboratory differentiation between celiac disease and gluten immune reactivity/sensitivity/autoimmunity are shown in Tables 7-9.

ii. Pattern of IgG, IgM and IgA Antibody Against Intestinal, BBB Proteins and Associated Antigens in Patients with Celiac Disease and Gut Permeability, Gluten Ataxia, and Patients with MS.

Based on the calculation of indices, the pattern of IgG, IgM and IgA antibodies in the nine healthy control subjects (Tables 1-3), 3 patients with celiac disease and gut permeability (Table 4), 3 patients with gluten ataxia (Table 5), and 3 patients with multiple sclerosis (Table 6) is shown in Tables 1-6, respectively. Note that in all healthy subjects, other than LPS and MBP, the antibody indices of which may be higher than 1.5 but not significantly greater than 2.0, the antibody indices against other antigens are lower or much lower than 1.5 (Tables 1-3).

In patients with celiac disease as confirmed by IgG and IgA against deamidated α-gliadin 33-mer peptide, tissue transglutaminase (tTg), and gliadin-tTg complex, the pattern of antibody varies from patient to patient.

For example, Sample 10 in Table 4, these antibodies are significantly elevated against LPS, zonulin/occludin, intestinal ZOT receptor, cell junction protein, MMP-3, α-B crystallin, and myelin basic protein, indicating that in addition to enhanced gut permeability the patient may be suffering from BBB permeability. Sample 11 in Table 4 shows significant elevation of antibodies against cell junction protein and intestinal ZOT receptor, and moderate elevation against LPS, but not against BBB proteins and neural antigens, indicating that in addition to celiac disease the patient may be suffering from intestinal permeability, BBB permeability, neuroautoimmunity, and possibly other autoimmunities.

The level of IgG, IgM and IgA antibodies against 12 different antigens representing gut-to-brain in 3 patients (Samples 13-15) with gluten ataxia is shown in Table 5. Gluten ataxia in these patients was confirmed by the presence of IgG and IgA antibodies against deamidated α-gliadin 33-mer peptide, tTg-2, gliadin-tTg complex, tTg-6 and cerebellar antigens. In these patients the pattern of antibodies was significantly higher against ZOT-binding protein, brain ZOT receptor, α-B crystallin, calprotectin, GFAP, and cell junction protein, confirming barrier damage impairment.

The level of these antibodies against 12 tested antigens in 3 patients (Samples 16-18) with MS is summarized in Table 6. In addition to an abnormal MRI, a diagnosis of MS was made based on antibody detection against MBP, myelin oligodendrocyte glycoprotein (MOG), α-B crystallin, proteolipid protein, lymphocyte activation and proinflammatory cytokine production (44). Significant elevation in the level of antibodies was detected against neuronal antigens, BBB proteins and zonulin/occludin. This is indicative that indeed patients with MS suffer from BBB dysfunction.

iii. Measurement of IgG, IgM and IgA Antibodies Against Bacterial Lipopolysaccharide and Occludin/Zonulin in Patients with Gastric Autoimmunity.

Figure 9:
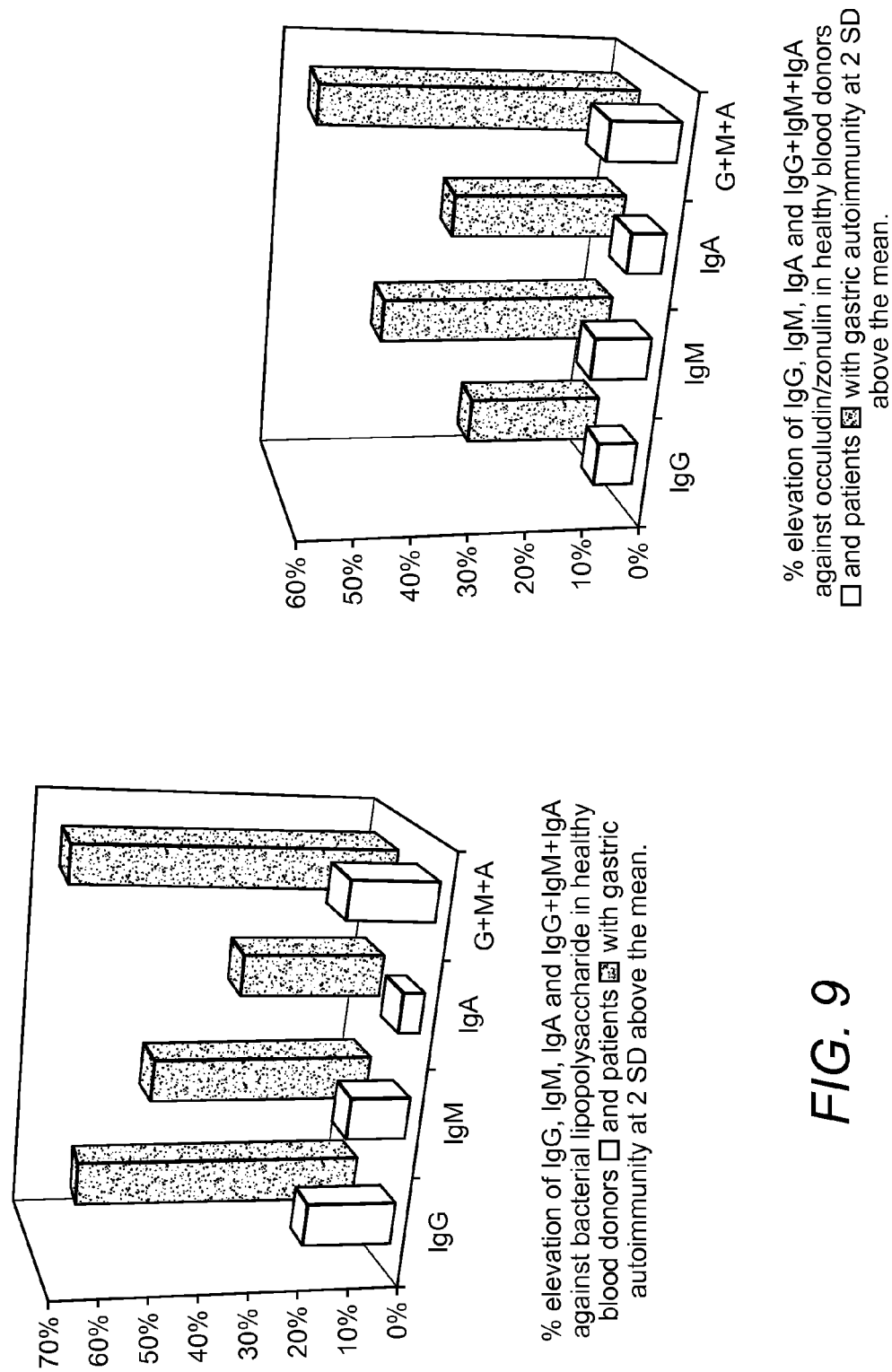
FIG. 9 is a diagram showing a comparison of IgG, IgM and IgA against bacterial lipopolysaccharide and occludin/zonulin in healthy donors and patients with gastric autoimmunity. The percent elevation of IgG, IgM, IgA and IgG+IgM+IgG against bacterial lipopolysaccharide in healthy donors shown in the light bars in the graph on the left and patients with gastric autoimmunity at two standard-deviations above the mean shown in the dark bars in the graph on the left. The percent elevation of IgG, IgM, IgA and IgG+IgM+IgG against occluding/zonulin in healthy donors shown in the light bars in the graph on the right and patients with gastric autoimmunity at two standard-deviations above the mean shown in the dark bars in the graph on the right.

Intestinal permeability is significant in gastrointestinal autoimmune disease (4). FIG. 9 shows diagrams that compare the elevation of antibodies against bacterial endotoxins (lipopolysaccharides) and the structure of the tight junctions (occludin/zonulin) in healthy controls and patients with gastric autoimmunity.

The exaggerated entrance of antigenic macromolecules across the gut epithelium can initiate production of, and perpetuate an ongoing increase in, multiple inflammatory cytokines and systemic chronic inflammation (56). This appears to be a required component for the trio of factors that lead to eventual autoimmune disease (genetic vulnerability, environmental exposure, and intestinal permeability).

According to certain aspects of the present invention, it is hypothesized herein that elevated antibodies to LPS, occludin/zonulin and the actomyosin network are biomarkers identifying the breakdown of a healthy intestinal barrier, and that elevated antibodies to LPS, occludin/zonulin, other cell junction proteins, BBB proteins plus neural antigens (for example, MBP, α-B crystalline, GFAP, calprotectin, and brain ZOT protein) not only indicate the breakdown of a healthy intestinal barrier, but also a failure in BBB integrity.

Clinical interpretation of elevated level of antibodies against LPS, occludin/zonulin and actomyosin in oral fluid according to certain aspects of the present invention is shown in Table 8.

Clinical interpretation of elevated blood level of antibodies against LPS, occludin/zonulin, blood brain barrier protein and neural antigens according to certain aspects of the present invention is shown in Table 9.

CASE STUDY EXAMPLES

Two different case reports, the first on a patient with celiac disease and the second with multiple sclerosis are provided as follows.

A. Case Report #1

Patient with Celiac Disease and Intestinal Barrier Dysfunction

A 38 year-old woman 5'4" in height weighing 106 lbs with GI disorder including constipation, diarrhea and pain all over the body, with fibromyalgia-like syndrome and loss of weight (1-2 lbs per month during the last six months) was examined by an internist. Lab investigation revealed abnormal CBC with hemoglobin of 9.9 g/dl, MCV of 77 fL, erythrocyte sedimentation rate of 54 mm/1$^{st}$ hr, with low concentration of folate and vitamin B-12 but high level of liver enzymes and high sensitive C-reactive protein. Detailed biochemical and immunological profiles including ANA, rheumatoid factor, T3, T4 and TSH levels were performed and all tests were within the normal range. After repeated complaints about GI discomfort, low-grade fever and headache, the patient was referred for GI evaluation. Colonoscopy and duodenal biopsy were performed and immunohistological evaluation revealed total villous atrophy with Marsh III classification. At this point IgG and IgA concentrations against gliadin and transglutaminase were checked. Both IgG and IgA against gliadin and transglutaminase were 3-5 fold higher than the reference range.

In view of the villous atrophy, gliadin and transglutaminase positivity diagnosis of celiac disease was made. The patient was transfused with blood, put on anti-inflammatory medication and started on a gluten-free diet. Three months later, although her overall GI discomfort had improved and she had gained 4 pounds, her CRP was still elevated, and the body ache and low-grade fever continued. In view of this and to determine the root cause of the inflammation and low-grade fever, antibodies against LPS, zonulin/occludin, and cell junction proteins were examined. Results presented in Table 4, Sample 10 showed that in comparison to healthy subjects, the patient (Sample 10) had a 3-6 fold increase in IgG, IgM and IgA antibody levels against LPS, zonulin/occludin and cell junction proteins, indicating that in addition to celiac disease the patient was suffering from bacterial translocation, tight junction damage and leaky gut syndrome to large antigenic molecules.

Accordingly, in addition to the gluten-free diet, the patient was treated for leaky gut syndrome with the implementation of a lectin-free diet plus probiotics glutamine, N-acetylcysteine, EPA/DHA, vitamin D, lactoferrin, xylitol, and boswellic acid. Thirty days after commencement of this probiotic regimen plus the lectin- and gluten-free diet, the patient's clinical condition had improved significantly: her fever was down to 37° C. and she had gained an additional 6 lbs. Sixty days later the treatment for leaky gut was reduced to probiotics only, but the gluten-free diet was continued. One year later all lab tests were repeated, and the repeat tests for gliadin, transglutaminase, CRO, LPS, and zonulin/occludin were within the normal range, which was a further indication that management for leaky gut plus a gluten-free diet was effective in the treatment of this patient who suffered from celiac disease and leaky gut syndrome.

Discussion: It has been established in the literature that in addition to villous atrophy the majority of patients with celiac disease also suffer from leaky gut syndrome. For this reason, approximately only 50% of patients with celiac disease improve on a gluten-free diet, with the structure of their villi returning to normal after six months of such treatment. The mechanism by which leaky gut syndrome is induced in celiac disease is due to the fact that in some individuals specific gliadin peptides bind to the epithelial cell and cause damage to the tight junction proteins, causing the release of zonulin/occludin and claudins from the submucosa into the blood. In this particular case, some of the patient's symptomatologies improved on the gluten-free diet, but the gluten-free diet did not ameliorate the inflammatory cascade induced by the LPS translocation and enhanced gut permeability. However, 30-90 days after implementation of the gluten-free diet plus treatment for repairing the tight junction proteins using natural remedies (57-61), both clinical symptomatologies and lab test results were back to normal. Thus, it is concluded that patients with celiac disease should be screened for leaky gut for large molecules that are antigenic, and treated not only for celiac disease but also for repairing the gut barrier. The inventive subject matter of the present invention provides for this capability.

B. Case Report #2

Patient with Multiple Sclerosis, Gut and Blood-Brain Barrier Permeability

A 38 year-old man 5'8" in height weighing 182 lbs following a 3-week history of progressive neck, back and muscle pain with weakness of the limbs was referred to a neurologist. On the day prior to referral, he developed difficulty in passing urine with tingling and sensory disturbance in his trunk and legs to a degree where he was unable to climb stairs. Just over two years prior to admission, the patient had family problems and had become very depressed, for which he had not sought any help. His overall past history was otherwise unremarkable except for unexplained mild microcytic anemia which had been treated with vitamin B-12 and iron supplements.

To clarify whether or not the patient may have suffered from a minor stroke or was suffering from some neurological or autoimmune disorder, a series of immunological profiles and neurological examinations was initiated.

Lab investigation revealed normal chemistry and CBC with a hemoglobin result of 10.8 g/dl. The immunological profile including ANA, rheumatoid factor, immune complexes, total immunoglobulins, cardiolipid antibodies and thyroid function tests were within the normal range.

During further investigation cerebrospinal fluid and blood was collected and examined for mycobacteria, Borrelia, CMV, EBV, Herpes Type-6, HTLV-1 and -2, and syphilis, all of which were negative. CSF protein was 0.7 g/L, and glucose 2.3 mMol/L.

Neurological examination revealed reduced corrected visual acuity of 6/48 in the right eye and 6/36 in the left eye with normal eye movements. The patient had pyramidal weakness in both legs with mildly-based gait. Pinprick examination demonstrated hemisensory level below D10 on both sides.

An MRI scan of the brain showed mild white matter abnormalities with mild generalized atrophy, which has been observed in patients with MS.

However, to exclude the possibility of gluten sensitivity, celiac disease and leaky gut syndrome, AGA, tTg antibody, and lactulose/mannitol tests were performed. A celiac screen revealed both IgG and IgA anti-gliadin antibodies 3-6 fold above the reference range but was completely negative for IgG and IgA against transglutaminase. In addition, the lactulose/mannitol test result was highly abnormal. Consequently, the following additional tests were performed: IgG, IgM and IgA antibody against LPS, zonulin/occludin, intestinal ZOT receptor, cell junction protein, MMP-3, brain ZOT binding protein, brain ZOT receptor, calprotectin, GFAP, α-B crystallin, BBB protein, and MBP. Results summarized in Table 6, Sample 17 show a significant elevation in antibody levels against MBP and GFAP, confirming the abnormal MRI findings and a diagnosis of MS. Furthermore, a significant elevation of antibodies against zonulin/occludin, calprotectin and BBB protein indicated involvement of the GI tract with enhanced gut and BBB permeability in this patient (Table 6). Based on these test results, the patient was given 1 g intravenous methylprednisolone for five days with some resultant clinical improvement. At this point the patient was put on β-seron, showing significant improvement fifteen days later. Furthermore, 200 mg of minocycline IV glutathione, plus probiotics glutamine, N-acetylcysteine, EPA/DHA, vitamin D, lactoferrin, xylitol, and boswellic acid were given for repairing the damaged BBB and gut barriers. Three months after this regimen the patient's overall health had improved significantly.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

1. Walker W A, Sanderson I R. Epithelial barrier function to antigens. *Ann NY Acad. Sci.* 664: 10-17, 1992.
2. Walker W A, Isselbacher K J. Uptake and transfer of macromolecules by the intestine. *Gastroenterol.* 67: 531-550, 1974.
3. Arrieta M C, Bistritz L, Meddings J B. Alterations in intestinal permeability. *Gut.* 55: 1512-1520, 2006.
4. Fasano A, Shea-Donohue T. Mechanisms of disease: the role of intestinal barrier function in the pathogenesis of gastrointestinal autoimmune diseases. *Nat Clin Prac Gastroenterol Hepatol.* 2(9): 416-422, 2005.
5. Sapone A, Lammers K M, Mazzarella G, et al. Differential mucosal IL-17 expression in two gliadin-induced disorders: gluten sensitivity and the autoimmune enteropathy celiac disease. *Int Arch Allergy Immunol.* 152: 75-80, 2010.
6. Sapone A, Lammers K M, Casolaro V, et al. Divergence of gut permeability and mucosal immune gene expression in two gluten-associated conditions: celiac disease and gluten sensitivity. *BMC Med.* 9: 23, 2011.
7. Fasano A. Zonulin and its regulation of intestinal barrier function: the biological door to inflammation, autoimmunity and cancer. *Physiol Rev,* 91: 151-175, 2011.
8. Shor D B, Barzilai O, Ram M, et al. Gluten sensitivity in multiple sclerosis: experimental myth or clinical truth? *Ann NY Acad Sci,* 1173: 343-349, 2009.

9. Vojdani A, O'Bryan T, Green J A, et al. Immune response to dietary proteins, gliadin and cerebellar peptides in children with autism. *Nutr Neurosci.* 7(3):151-161, 2004.
10. Correale J, Villa A. The blood-brain-barrier in multiple sclerosis: functional roles and therapeutic targeting. *Autoimmunity.* 40: 148-160, 2007.
11. Morgan L, Shah B, Rivers L E, et al. Inflammation and dephosphorylation of the tight junction protein occluding in an experimental model of multiple sclerosis. *Neurosci.* 147: 664-673, 2007.
12. Skardelly M, Armbruster F P, Meixensberger J, et al. Expression of zonulin, c-kit, glial fibrillary acidic protein in human gliomas. *Transl Oncol.* 2: 117-120, 2009.
13. Yacyshyn B, Meddings J, Sadowski D, et al. Multiple sclerosis patients have peripheral blood CD45RO+ B cells and increased intestinal permeability. *Dig Dis Sci.* 41(12): 2493-2498, 1996.
14. Garate I, Garcia-Bueno B, Madrigal, J L M et al. Origin and consequences of brain toll-like receptor 4 pathway stimulation in an experimental model of depression. *J Neuroinflamm.* 8:151, 1-31, 2011.
15. Al-Sadi R M, Ma T Y. IL-1β causes an increase in intestinal epithelial tight junction permeability. *J Immunol.* 178: 4641-4649, 2007.
16. Matysiak-Budnik T, Thomas-Collignon A, Megraud F, Heyman M. Alterations of epithelial permeability by *Helicobacter* and IL-1beta in vitro: protective effect of rebamipide. *Dig Dis Sci,* 2001; 46:1558-1566.
17. Turner J R. "Putting the squeeze" on the tight junction: understanding cytoskeletal regulation. *Semin Cell Dev Biol,* 2000; 11:301-308.
18. Ma T Y, Hoa N T, Tran D D, Bui V, Pedram A, Mills S, Merryfield M. Cytochalasin B modulation of Caco-2 tight junction barrier: role of myosin light chain kinase. *Am J Physiol,* 2000; 279:G875-G885.
19. Ma T Y, Tran D, Hoa N, Nguyen D, Merryfield M, Tarnawski A. Mechanism of extracellular calcium regulation of intestinal epithelial tight junction permeability: role of cytoskeletal involvement. *Microsc Res Tech,* 2000; 51:156-168.
20. Al-Sadi R, Ye D, Dokladny K, Ma T Y. Mechanism of IL-1β-induced increase in intestinal epithelial tight junction permeability. *J Immunol.* 2008; 180:5653-5661.
21. Shen L, Black E D, Witkowski E D, Lencer W I, Guerriero V, Schneebrger E E, Turner J R. Myosin light chain phosphorylation regulates barrier function by remodeling tight junction structure. *J Cell Sci,* 2006; 119:2095-2106.
22. Hecht G, Pestic L, Nikcevic G, Koutsouris A, Tripuraneni J, Lorimer Dd, Nowak G, Guerriero, Jr V, Elson El, Lanerolle P D. Expression of the catalytic domain of myosin light chain kinase increases paracellular permeability. *Am J Physiol,* 1996; 271:C1678-1684.
23. Ma T Y, Boivin M A, Ye E, Pedram A, Said H M. Mechanism of TNF-α modulation of Caco-2 intestinal epithelial tight junction barrier: role of myosin light-chain kinase protein expression. *Am J Physiol,* 2005; 288:G422-G430.
24. Mae M, Kudera M, Leunis J C. The gut-brain barrier in major depression: intestinal mucosal dysfunction with an increased translocation of LPS from gram negative bacteria (leaky gut) plays a role in the inflammatory pathophysiology of depression. *Euro Endocrinol Lett,* 2008; 29:117-124.
25. Mae M, Coucke F, Ategis J C. Normalization of the increased translocation of endotoxin from gram negative enterobacteria (leaky gut) is accompanied by a remission of chronic fatigue syndrome. *Neuro Endocrinol Lett,* 2007; 28(6):101-116.
26. Walker-Smith J A, Ford R P, Phillips A D. The spectrum of gastrointestinal allergies to food. *Ann Allergy,* 1984; 53:629-636.
27. Juvonen P, Jakobsson I, Lindberg T. Macromolecular absorption and cow's milk allergy. *Arch Dis Child,* 1990; 65:300-303.
28. Huang X N, Fu J, Wang W Z. The effects of Fasudil on the permeability of the rat blood-brain barrier and blood-spinal cord barrier following experimental autoimmune encephalomyelitis. *J Neuroimmunol.* 239: 61-67, 2011.
29. Lassmann H, Zimprich F, Vass K, Hickey W F. Microglial cells are a component of the perivascular glia limitans. *J Neurosci Res,* 1991; 28:236-243.
30. Schneeberger E E, Lynch R D. The tight junction: a multifunctional complex. *Am J Physiol Cell Physiol,* 2004; 286:C1213-C1228.
31. Chen M L, et al. Disruption of tight junctions and induction of proinflammatory cytokine responses in colonic epithelial cells by *Campylobacter jejuni. Infect Immun,* 2006; 74:6581-6589.
32. LaPierre L A. The molecular structure of the tight junction. *Adv Drug Deliv,* 2000; 41:255-264.
33. Wong V, Gumbiner B M. A synthetic peptide corresponding to the extracellular domain of occludin perturbs the tight junction permeability barrier. *J Cell Biol,* 1997; 136 (2):399-409.
34. Engelhardt B, Rasohoff R M. The ins and outs of the T-lymphocyte trafficking to the CNS: anatomical sites and molecular mechanisms. *Trends Immunol,* 2005; 26(9):485-495.
35. Aloisi F, Ria F, Adorini L. Regulation of T-cell responses by CNS antigen-presenting cells: different roles for microglia and astrocytes. *Immunol Today,* 2000; 21(3):141-147.
36. Ghirnikar R S, Lee Y L, Eng L F. Inflammation in traumatic brain injury: role of cytokines and chemokines. *Neurochem Res,* 1998; 23(3):329-340.
37. Kebir H, Kreymborg K, Ifergan I, Dodelet-Devillers A, Cayrol R, Bernard M, Biuliani F, Arbour N, Becher B, Prat A. Human TH17 lymphocytes promote blood-brain barrier disruption and central nervous system inflammation. *Nat Med,* 2007; 13:1173-1176.
38. Sospedra M, Martin R. Immunology of multiple sclerosis. *Annu Rev Immunol,* 2005; 23:683-747.
39. Biernacki K, Prat A, Blain M, Antel J P. Regulation of Th1 and Th2 lymphocyte migration by human adult brain endothelial cells. *J Neuropathol Exp Neurol,* 2001; 60(12): 1127-1136.
40. Wosik K, Cayrol R, Dodelet-Devillers A, Berthelet F, Bernard M, Moumdjian R, Bouthillier A, Reudelhuber T L, Prat A. Angiotensin II controls occluding function and is required for blood-brain barrier maintenance: relevance to multiple sclerosis. *J Neurosci,* 2007; 27(34):9032-9042.
41. Kawanokuchi J, Shimizu K, Nitta A, Yamada K, Mizuno T, Takeuchi H, Suzumura A. Production and function of IL-17 in microglia. *J Neuroimmunol,* 2008; 194:54-61.
42. Ganor Y, Teichberg V I, Levite M. TCR activation eliminate glutamate receptor GLUR3 from the cell surface of normal human T cells via an autocrine/paracrine granzyme B-mediated proteolytic cleavage. *J Immunol,* 2007; 178: 683-692.
43. Vojdani A, Lambert J. A gut feeling for immune dysregulation and neuroinflammation. *The Autism File USA,* 2009; 31: 56-64.
44. Vojdani A, Vojdani E, Cooper E L. Antibodies to myelin basic protein, myelin oligodendrocytes peptides, α-β-crys- 45. Kirk J, Plumb J, Mirakhur M, et al. Tight junctional abnormality in multiple sclerosis white matter affects all calibers of vessel and is associated with blood-brain barrier leakage and active demyelination. *J Pathol.* 2003; 201: 319-327.
46. Hawkins B T, Davis T P. The blood-brain barrier/neurovascular unit in health and disease. *Pharmacol Rev,* 2005; 57: 173-185.
47. Leech S, Kirk J, Plumb J, et al. Persistent endothelial abnormalities and blood-brain barrier leak in primary and secondary progressive multiple sclerosis. *Neuropathol Appl Neurobiol,* 2007; 33: 86-98.
48. Persidsky Y, Ramirez S H, Haorah J, et al. Blood-brain barrier: structural components and function under physiologic and pathologic conditions. *J Neuroimmune Pharmacol,* 2006, 1: 223-236.
49. Reijerkerk A, Kooij G, van der Pol S M, et al. Tissue-type plasminogen activator is a regulator of monocyte diapedesis through the brain endothelial barrier. *J Immunol,* 2008; 181: 3567-3574.
50. Wosik K, Cayrol R, Dodelet-Devillers A, et al. Angiotensin II controls occludin function and is required for blood-brain barrier maintenance: relevance to multiple sclerosis. *J Neurosci,* 2007; 27: 9032-9042.
51. El Asmar, Panigrahi P, Bamford P, et al. Host-dependent zonulin secretion causes the impairment of the small intestine barrier function after bacterial exposure. *Gastroenterol,* 2002; 123: 1607-1615.
52. Balkovetz D F, Katz J. Bacterial invasion of paracellular route: divide and conquer. *Microbes Infect,* 2003; 5:613-619.
53. Kuula H et al. Local systemic responses in matrix metalloproteinase 8-deficient mice during *Porphyromonas gingivalis*-induced periodontitis. *Infect Immun,* 2009; 77(2): 850-859.
54. Cywes C., Wessels M. R. Group A *Streptococcus* tissue invasion by CD44-mediated cell signalling. *Nature,* 2001; 414:648-652.
55. Y Xu, Q Yu. E-cadherin negatively regulated CD44-hyaluronan interaction and CD44-mediated tumor invasion and branching morphogenesis. *J Biol Chem,* 2003; 278: 8661-8668.
56. Garrote J, Gomez-Gonzalez E, Bernardo D, Arranz E, Chirdo F. Celiac disease pathogenesis: the proinflammatory cytokine network. *J Pediatr Gastroenterol Nutr,* 2008; 47(Suppl 1).
57. Maldonado Galdeano C, Perdigon G. The probiotic bacillum *Lactobacillus casei* induces activation of the mucosal immune system through innate immunity. *Clin Vaccine Immunol,* 2006, 13(2):219-226.
58. Wakabayashi H, Takakura N, Yamauchi K, et al. Modulation of immunity-related gene expression in small intestine of mice by oral administration of lactoferrin. *Clin Vaccine Immunol,* 2006; 13(2):239-245.
59. Han S, Jeong S Y, Nam Y J, et al. Xylitol inhibits inflammatory cytokine expression induced by lipopolysaccharides from *Porphyromonas gingivalis. Clin Diag Lab Immunol,* 2005; 12(11):1285-1291.
60. Chevrier M R, Ryan A E, Lee D Y-W, et al. *Boswellia carterii* extract inhibits the cytokines and promotes Th2 cytokines in vitro. *Clin Diag Lab Immunol,* 2005; 575-580.
61. Syrovets T, Büchele B, Krauss C, et al. Acetyl-boswellic acids inhibit lipopolysaccharide-mediated TNF-alpha induction in monocytes by direct interaction with IκB kinases. *J Immunol,* 2005; 174: 498-506.

The invention claimed is:

1. A test plate having separate test areas for bound peptides including: (1) a lipopolysaccharide; and (2) a native antigen comprising at least one of (a) a gut-related antigen and (b) a blood brain barrier-related antigen.

2. The test plate of claim 1, wherein the gut-related antigen is selected from the list consisting of: (1) an intestinal structural protein; (2) a tight junction protein; and (3) a binding receptor to the tight junction protein; (4) a cell junction protein.

3. The test plate of claim 2, wherein the blood brain barrier-related antigen is selected from the list consisting of: (1) a blood brain barrier protein; (2) a glial fibrillary acidic protein (GFAP); (3) matrix metalloproteinase (MMP), (4) a brain ZOT binding protein; (5) brain ZOT receptor; (6) a calprotectin; and (7) a myelin basic protein.

4. The test plate of claim 1, wherein the blood brain barrier-related antigen is selected from the list consisting of: (1) a blood brain barrier protein; (2) a glial fibrillary acidic protein (GFAP); (3) matrix metalloproteinase (MMP), (4) a brain ZOT binding protein; (5) brain ZOT receptor; (6) a calprotectin; and (7) a myelin basic protein.

* * * * *